United States Patent [19]

Ajito et al.

[11] Patent Number: 5,444,174
[45] Date of Patent: Aug. 22, 1995

[54] 16-MEMBERED MACROLIDE DERIVATIVE HAVING SUSTAINED ANTIBACTERIAL ACTIVITY IN PLASMA, SYNTHESIS INTERMEDIATE THEREOF AND PROCESS FOR PRODUCING THE SAME

[75] Inventors: Keiichi Ajito; Kenichi Kurihara; Tsuneo Ishizuka; Tetsuro Hara; Takayuki Usui; Seiji Shibahara, all of Kanagawa, Japan

[73] Assignee: Meiji Seika Kaisha, Ltd., Tokyo, Japan

[21] Appl. No.: 22,165

[22] Filed: Feb. 25, 1993

[30] Foreign Application Priority Data

Feb. 26, 1992 [JP] Japan .................................. 4-039013
Jan. 13, 1993 [JP] Japan .................................. 5-004389

[51] Int. Cl.⁶ ..................... C07H 17/08; C07D 313/06
[52] U.S. Cl. .................................. 536/7.1; 536/17.2; 536/16.8; 549/270; 549/271
[58] Field of Search .......................... 536/9, 17, 18, 7.1

[56] References Cited

U.S. PATENT DOCUMENTS

4,255,564  3/1981  Umezawa et al. ................. 536/17 R

FOREIGN PATENT DOCUMENTS

0177696  4/1986  European Pat. Off. .
0290203  4/1988  European Pat. Off. .
58998    4/1985  Japan .
234093  10/1987  Japan .

OTHER PUBLICATIONS

Mallams et al. *J. Chem. Soc. Perkin Trans I*, pp. 799–805, (1989).
Japanese Journal of Antibiotics, 35(6), pp. 1462–1474 (1982).
Chemical Letters, pp. 769–772 (1977).
Yakugaku Zasshi, 102(8), 781–795 (1982).
The Journal of Antibiotics, 24(7), pp. 452–459 (1971).
The Journal of Antibiotics, 24(7), pp. 476–490 (1971).
The Journal of Antibiotics, 24(8), pp. 526–536 (1971).
The Journal of Antibiotics, 28(10), pp. 789–797 (1975).
The Journal of Antibi tics, 29(5), pp. 536–548 (1976).
The Journal of Antibiotics, 32(7), pp. 777–779 (1979).
Carbohydrate Research, 54, pp. 85–104 (1977).
Journal of the American Chemical Society, 96(9), pp. 2829–2835 (1974).
Journal of the American Chemical Society, 99(7), pp. 5826–2857 (1977).
T. Sato et al., Difference in Physico-Pharmaceutical Properties Between Crystalline and Monocrystalline 9,3″-diacetylmidecamycin, *Chemical Pharmaceutical Bulletin*, vol. 29, No. 9, 1981, pp. 2675–2682.

*Primary Examiner*—Douglas W. Robinson
*Assistant Examiner*—Howard C. Lee
*Attorney, Agent, or Firm*—Sughrue, Mion, Zinn, Macpeak & Seas

[57] ABSTRACT

16-membered macrolide compounds wherein both of hydroxyl groups at the 3″- and 4″-positions form ether bonds together with two alkyl groups which are either the same or different from each other is useful as an antibacterial agent. The macrolide compounds represented by formula (I) are prepared by chemically modifying midecamycin $A_3$ to obtain a synthesis intermediate of the formula (II), which is further chemically modified.

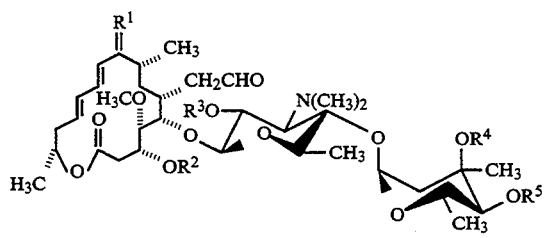

(I)

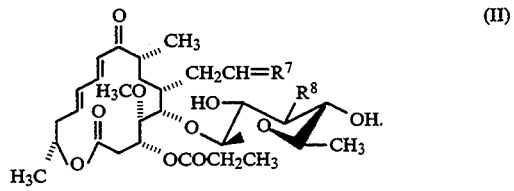

(II)

13 Claims, 1 Drawing Sheet

16-MEMBERED MACROLIDE DERIVATIVE HAVING SUSTAINED ANTIBACTERIAL ACTIVITY IN PLASMA, SYNTHESIS INTERMEDIATE THEREOF AND PROCESS FOR PRODUCING THE SAME

FIELD OF THE INVENTION

This invention relates to 16-membered macrolide derivatives, which are effective on gram-positive bacteria and exert a sustained antibacterial effect in plasma, an important synthesis intermediate thereof and a process for producing the same.

BACKGROUND OF THE INVENTION

Macrolide antibiotics which are effective for gram-positive bacteria, Mycoplasma and Chlamydia are regarded as important antibacterial agents from a clinical viewpoint, since they can be orally administered and show a low toxicity. Among these antibiotics, marketed 16-membered macrolide antibiotics are advantageous in that, for example, the tolerance thereof is scarcely induced and they exert little interaction with other drugs compared with 14-membered ones and scarcely affect the intestinal tract. Thus, they have been widely employed all over the world, mostly, in Asian countries. In particular, miokamycin, which is superior in the dynamics in vivo to natural compounds and has a relieved bitterness [Journal of Antibiotics, 29(5), 536 (1976)]; Japanese Journal of Antibiotics, 35(6), 1462 (1982)] has been frequently employed as a semisynthetic 16-membered macrolide antibiotic for clinical purposes.

In order to improve the antibacterial activity and/or the dynamics in vivo of 16-membered macrolides, a number of derivatives wherein some of the hydroxyl groups thereof are acylated have been synthesized. On the other hand, several groups of workers have already reported the synthesis of 16-membered macrolide derivatives wherein hydroxyl groups in the mycarose moiety are monoalkylated [Chemistry Letters, p. 769 (1977); JP-A-60-58998; and JP-A-62-234093; the term "JP-A" as used herein means an "unexamined published Japanese patent application"].

Miokamycin, which is a newly marketed 16-membered macrolide antibiotic, is superior to midecamycin in infection-protective action in vivo and recovery ratio in urine, but it is not fully satisfactory. Shomura et al. reported that an acyl group at the mycarose moiety of miokamycin is eliminated in vivo and, as a result, the antibacterial activity of this antibiotic is reduced, which is one of factors interfering the embodiment of its excellent dynamics in vivo [Yakugaku Zasshi, 102(8), 781 (1982)]. It is, therefore, required to develop a 16-membered macrolide derivative which remains stable in vivo and scarcely suffers from any decrease in antibacterial activity when metabolized.

SUMMARY OF THE INVENTION

An object of the present invention is to provide a 16-membered macrolide derivative which shows improved properties from the clinical viewpoint.

In order to satisfy the above-mentioned requirement, the present inventors have conducted synthetic chemical studies and, as a result, succeeded in the synthesis of a novel derivative wherein two hydroxyl groups in the mycarose moiety of a 16-membered macrolide derivative form both ether bonds together with two alkyl groups. They have further found out that such a derivative shows clinically important properties such as strong inhibitory activity against the growth of gram-positive bacteria and an antibacterial activity sustained for a extremely long period of time in rat plasma.

Accordingly, the first gist of the present invention relates to a novel compound represented by the following formula (I):

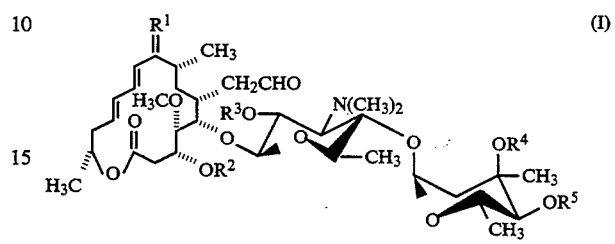

wherein $R^1$ represents an oxygen atom, a hydroxyl group and a hydrogen atom or a group of the formula $OCOR^6$, wherein $R^6$ represents a straight chain alkyl group having 1 to 3 carbon atoms, and a hydrogen atom, $R^2$ represents a hydrogen atom or a group of the formula $COR^6$, wherein $R^6$ is as defined above, $R^3$ represents a hydrogen atom or a group of $COR^6$, wherein $R^6$ is as defined above, $R^4$ represents a straight chain alkyl group having 1 to 4 carbon atoms, and $R^5$ represents a substituted or unsubstituted straight chain or branched alkyl or aralkyl group having 1 to 10 carbon atoms, or a pharmaceutically acceptable salt thereof.

The second gist of the present invention relates to a compound represented by the following formula (II), which is an important intermediate for synthesis of the compound of the formula (I):

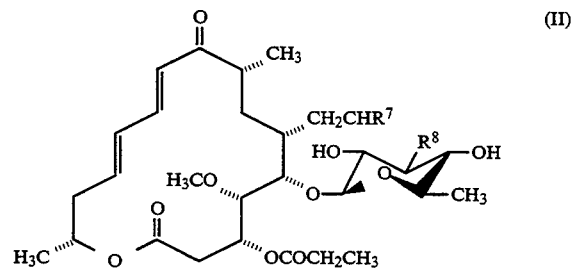

wherein $R^7$ represents an oxygen atom, a ring structure of the formula $-O(CH_2)_nO-$, wherein n is an integer of 2 or 3, a group of the formula $=(OR^9)_2$, wherein $R^9$ represents an alkyl group having 1 to 4 carbon atoms or a benzyl group, a ring structure of the formula $-S(CH_2)_nS-$, wherein n is an integer of 2 or 3, or a group of the formula $=(SR^9)_2$, wherein $R^9$ is as defined above, and $R^8$ is a dimethylamino group or a dimethylamino group N-oxide provided that $R^8$ is not a dimethylamino group when $R^7$ is an oxygen atom, or a salt thereof.

DETAILED DESCRIPTION OF THE INVENTION

Figure 1:
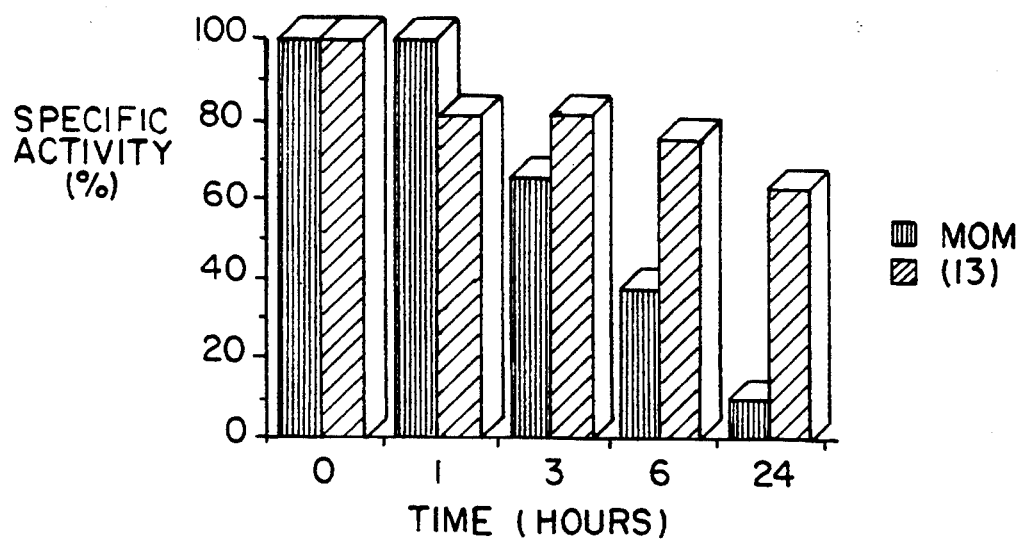
FIG. 1 shows changes in the antibacterial activities of miokamycin (MOM) and the compound (13) against *M. luteus* in thawed rat plasma with the lapse of time in terms of specific activity expressed by referring the starting activity of each compound in the plasma to as 100%.

A process for producing compounds of the formulae (I) and (II) is described below.

An example of the process of the present invention is shown in the following reaction schemes 1-1 and 1-2. The reaction schemes 1-1 and 1-2 relate to the production of the compound of the formula (I) wherein $R^1$ is an oxygen atom, $R^2$ is a propionyl group, $R^3$ is a hydrogen atom and $R^4$ is a methyl group using the compound of the formula (II) wherein $R^7$ is an ethylenedioxy group and $R^8$ is a dimethylamino group, but the present invention is not to be limited thereto.

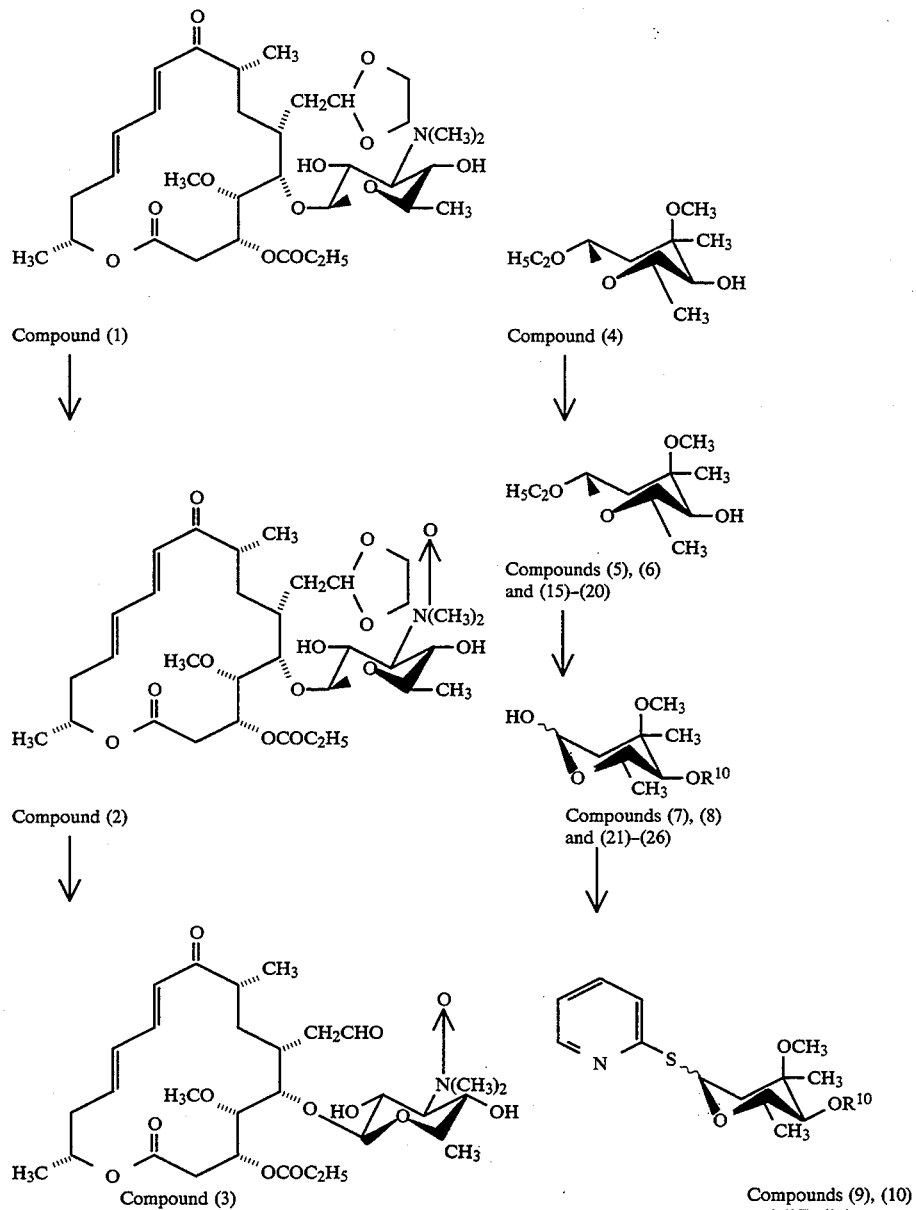

Reaction scheme 1-1

Compounds (5), (7) and (9), $R^{10}$: $CH_2CH_3$
Compounds (6), (8) and (10), $R^{10}$: $CH_2CH_2CH(CH_3)_2$
Compounds (15), (21) and (27), $R^{10}$: $CH_2CH=CH_2$
Compounds (16), (22) and (28), $R^{10}$: $CH_2CH=C(CH_3)_2$
Compounds (17), (23) and (29), $R^{10}$: $CH_2(CH_2)_2CH_3$
Compounds (18), (24) and (30), $R^{10}$: $CH_2(CH_2)_4CH_3$
Compounds (19), (25) and (31), $R^{10}$: $CH_2(CH_2)_2CH(CH_3)_2$
Compounds (20), (26) and (32), $R^{10}$: $CH_2C_6H_5$.

Reaction scheme 1-2

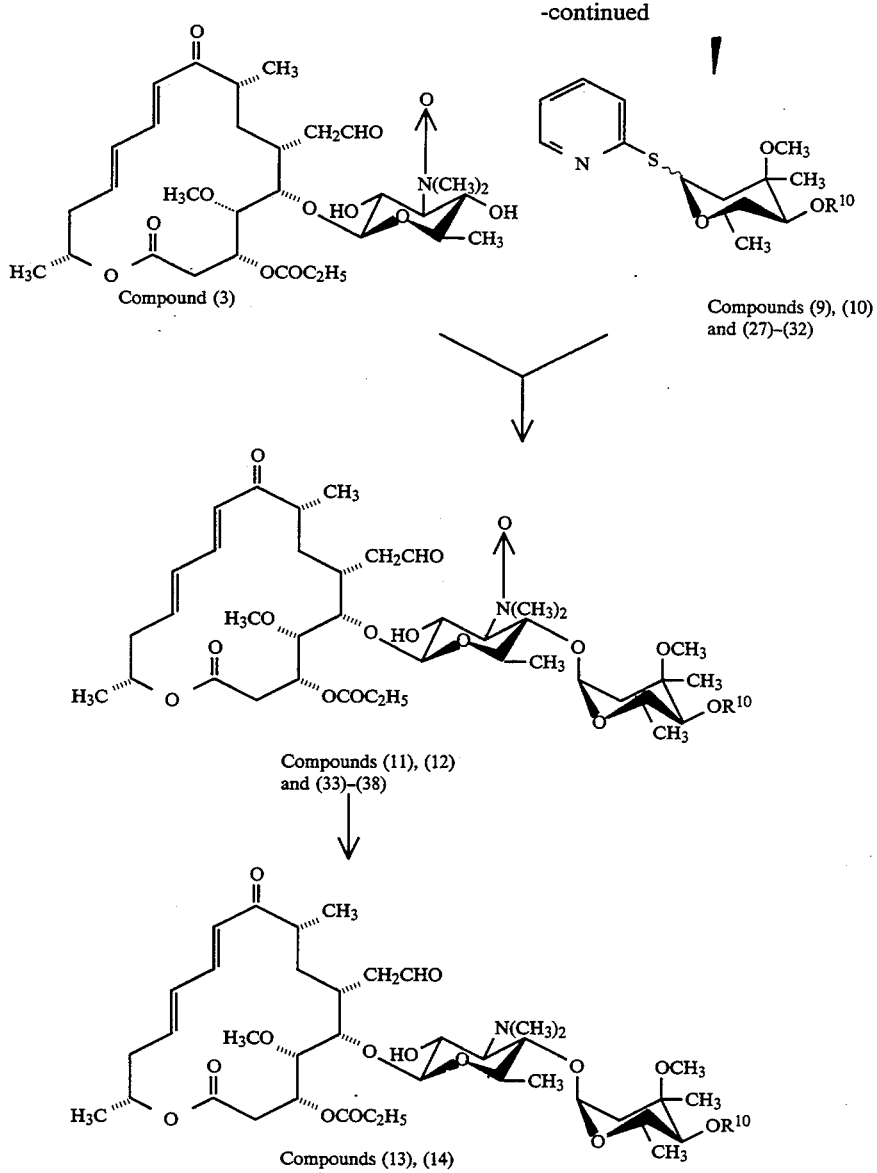

Compounds (9), (11) and (13), $R^{10}$: $CH_2CH_3$
Compounds (10), (12) and (14), $R^{10}$: $CH_2CH_2CH(CH_3)_2$
Compounds (27), (33) and (39), $R^{10}$: $CH_2CH=CH_2$
Compounds (28), (34) and (40), $R^{10}$: $CH_2CH=C(CH_3)_2$
Compounds (29), (35) and (41), $R^{10}$: $CH_2(CH_2)_2CH_3$
Compounds (30), (36) and (42), $R^{10}$: $CH_2(CH_2)_4CH_3$
Compounds (31), (37) and (43), $R^{10}$: $CH_2(CH_2)_2CH(CH_3)_2$
Compounds (32), (38) and (44), $R^{10}$: $CH_2C_6H_5$.

A process for producing a synthesis intermediate which is necessary for providing a novel, useful 16-membered macrolide derivative is described below with reference to the reaction scheme 1-1.

Midecamycin $A_3$ to be used as a starting substance is a known compound [Journal of Antibiotics, 24(7), 476 (1971)] and can be obtained by incubating *Streptomyces mycarofaciens*. Alternatively, it can be obtained by selectively oxidizing a hydroxyl group at the 9-position of midecamycin which is also a known compound [Journal of Antibiotics, 24(7), 452 (1971) and ibid., 24(8), 526 (1971)]. First, midecamycin $A_3$ is treated with an acid catalyst in the presence of ethylene glycol and thus the acylated mycarose moiety is cleaved to obtain a compound (1) which is a compound of the formula (II) wherein $R^7$ is an ethylenedioxy group and $R^8$ is a di-methylamino group. Usable as the acid catalyst are p-toluenesulfonic acid, benzenesulfonic acid, methanesulfonic acid, sulfuric acid and hydrochloric acid. p-Toluenesulfonic acid is preferably used. As a solvent, acetonitrile and cyclic ethers such as dioxane or tetrahydrofuran may be used. This reaction can easily proceed at a temperature of $-10°$ to $50°$ C.

When 1,3-propanediol or a lower alcohol is used in place of the ethylene glycol in the above reaction, the corresponding cyclic acetal or dialkyl acetal can be easily formed. Alternatively, these alcohols may be replaced with various thiols to obtain the corresponding dithioacetals.

Then, the compound (1) is reacted with a peroxide to thereby convert the dimethylamino group into the N-oxide hereof to give a compound (2) which is a compound of the formula (II) wherein $R^7$ is an ethylenedioxy group and $R^8$ is a dimethylamino group N-oxide. Examples of the peroxide include organic peroxides such as m-chloroperbenzoic acid, perbenzoic acid and peracetic acid, hydrogen peroxide and hydroperoxides such as t-butyl hydroperoxide. It is preferable to use m-chloroperbenzoic acid. A solvent may be selected from among chloroform, methylene chloride, methanol, ether and t-butyl alcohol. This reaction proceeds within a short period of time at a temperature of $-10°$ to $50°$ C. The compound (2), wherein the aldehyde group and the dimethylamino group are each protected, is an excellent 16-membered macrolide intermediate since it is so stable as to be stored at room temperature for a prolonged period of time. The compounds (1) and (2) having an acetoxy group at the 3-position have been already reported [Journal of the American Chemical Society, 99(17), 5826 (1977)].

The ethylenedioxy group of the compound (2) is easily eliminated through acid-hydrolysis in an aqueous solvent and thus a compound (3) which is a compound of the formula (II) wherein $R^7$ is an oxygen atom and $R^8$ is a dimethylamino group N-oxide is obtained. The acid-hydrolysis may be preferably carried out by using a mixture of 0.5 to 1N hydrochloric acid and acetonitrile or dioxane. The reaction is suitably carried out at $0°$ to $50°$ C. for 1 hour to several days, preferably at about $30°$ C. for 10 to 20 hours. The compound (3), wherein the dimethylamino group is protected, does not require deprotection of the aldehyde at the 18-position after the completion of the desired chemical conversion. Thus, it is a highly useful synthesis intermediate for chemically modifying a hydroxyl group at the 4'-position. Alternatively, the compound (3) can be easily obtained by converting a dimethylamino group of 9-dehydro-demycarosyl platenomycin (DDM-PLM) [Journal of Antibiotics, 28(10), 789 (1975)] into a dimethylamino group N-oxide by the above-mentioned method.

The synthesis of a 2-deoxy-L-sugar having two ether bonds, which never occurs in nature, is described below.

Erythromycin is treated with an acid catalyst in the presence of ethanol and the 3-O-methylmycarose (cladinose) residue is obtained as its β-glycoside, i.e., a compound (4). Examples of the acid catalyst include p-toluenesulfonic acid, benzenesulfonic acid, methanesulfonic acid, sulfuric acid and hydrochloric acid, with p-toluenesulfonic acid being preferred. Examples of a solvent include acetonitrile and cyclic ethers such as dioxane or tetrahydrofuran. This reaction can easily proceed at a temperature of $-10°$ to $50°$ C. The alcohol to be added is not restricted to ethanol but lower, straight-chain or branched alcohols such as methanol and propanol may be used therefor. During this conversion reaction with the acid catalyst, a small amount of α-glycoside is also formed as a side product in addition to the main product, i.e., the β-glycoside, compound (4). However, it is not needed to separate this side product, since it exerts no undesirable effect in the subsequent steps.

Then, appropriate alkyl or aralkyl side chains are introduced into free hydroxyl groups of the compound (4) to produce an L-sugar having two ether bonds. Namely, the compound (4) is reacted with sodium hydride to thereby convert the hydroxyl group at the 4-position into a sodium alkoxide. Then it is further reacted with ethyl iodide or isoamyl iodide as an alkylating agent to obtain 4-O-ethyl-3-O-methylmycaroside (4-O-ethylcladinoside) [compound (5)] or 4-O-isoamyl-3-O-methylmycaroside (4-O-isoamylcladinoside) [compound (6)], respectively. In order to form an alkoxide by eliminating a proton from a free hydroxyl group, sodium hydride may be replaced with other metal hydrides such as potassium hydride. The metal hydride is used in an amount of 1 mole to excess moles, preferably 2 to 5 moles per mole of the compound (4). Alkyl iodide to be used as an alkylating agent may be replaced with other alkyl halides such as alkyl bromides. Alkyl halide is used in an amount of 1 mole to excess moles, preferably 1 to 4 moles per mole of the compound (4). Examples of suitable alkyl moieties to be introduced are primary and secondary alkyl groups such as ethyl, isoamyl, allyl (2-propenyl), 3-methyl-2-butenyl, butyl, hexyl, 4-methylpentyl and benzyl with primary alkyl groups being particularly preferred. A solvent may be selected from among dimethylformamide, dimethyl sulfoxide and dioxane. These reactions can easily proceed at a temperature of $0°$ to $100°$ C. In these reactions, it is expected that the yield can be elevated by using a phase transfer catalyst or a mixture thereof.

Although cladinoside is used as a starting substance for forming the compounds (5) and (6) in the above-mentioned process and in the following Examples, various 3,4-di-O-alkylmycarosides including the compounds (5) and (6) can be produced by using mycaroside as a starting substance. Mycaroside has two free hydroxyl groups. One at the 3-position is a tertiary alcohol while another one at the 4-position is a secondary alcohol. It is, therefore, possible to use the difference in reactivity between these two hydroxyl groups in the etherification (Williamson's reaction). Thus, mycaroside is subjected to the above-mentioned etherification to give 4-O-alkylmycaroside and the resulting product is subjected to the second etherification to give 3,4-di-O-alkylmycaroside. Regarding Williamson's reaction into the tertiary alcohol at the second etherification, there has been established, for example, a method via a copper (I) tertiary alkoxide [Journal of the American Chemical Society, 96(9), 2829 (1974)].

Ethyl glycoside in the compound (5) or (6) is easily removed by acid hydrolysis in an aqueous solvent and thus a 2-deoxy reducing sugar [compound (7) or (8)] having two ether bonds is obtained. The acid hydrolysis is preferably carried out using a mixture of 0.5 to 1N hydrochloric acid and acetonitrile or dioxane. The reaction is carried out at $0°$ to $50°$ C. for 1 hour to several days, preferably at about $30°$ C. for 10 to 100 hours.

Then the non-natural type diether mycarose is converted into a glycosyl donor (i.e., a sugar source in a reaction for introducing sugar chain). In recent years, various attempts have been made to develop glycosylation methods in addition to conventional glycosylation methods using 1-halogen sugar (bromo sugar, chloro sugar). The attention is given to a method for introducing sugar chains by using 1-thio sugar, 1-fluoro sugar and 1-acyl sugar. Considering the final target compound in the present invention is a 2"-deoxy derivative, mycaral (a glycal derivative of mycarose) is also suitable as a glycosyl donor [Carbohydrate Research, 54, 85 (1977)]. The compounds (7) and (8) can be converted into all of the above-mentioned glycosyl donors, namely, 1-thio sugar, 1-fluoro sugar, 1-acyl sugar and glycal. Glycosylation processes using these compounds are applicable to the production of the compound of the formula (I) according to the present invention.

As an example of the production of a useful glycosyl donor, the synthesis of a 1-thio branched sugar [Journal of Chemical Society Perkin Transaction I, 1989, 799] is described below.

The compounds (7) and (8) are each reacted with aldrithiol-2 (2,2'-dipyridyl disulfide) and tri(n-butyl)-phosphine to respectively give 1-(2-pyridylthio) sugar, i.e., compounds (9) and (10). Aldrithiol-2 and tri(n-butyl)phosphine are suitably used in an amount of 1 mole to excess moles, preferably, 1.2 to 2 moles and 1.8 to 2.6 moles, per mole of the compound (7) or (8), respectively. Usable as a solvent are anhydrous methylene chloride, tetrahydrofuran, 1,2-dichloromethane and the like, with methylene chloride being preferred. The reaction is carried out at $-10°$ to $40°$ C. for 1 hour to 3 days, preferably at about $0°$ to $30°$ C. for 4 to 20 hours. These thio sugars are obtained each in the form of an almost equal-weight mixture of $\alpha$-thioglycoside with $\beta$-thioglycoside. However, effects of the configuration at the 1-position of a 1-thio sugar on the configuration of the anomeric carbon of a glycosylated product have never been fully clarified so far. Accordingly, these two 1-thio sugars anomers may be employed in the glycosylation reaction as a mixture without separating from each other. Examples of the 1-thio sugar include the above-mentioned 1-(2-pyridylthio) sugar, phenylthio sugar, methylthio sugar and thio sugar bound to heterocyclic rings other than pyridine ring.

The introduction of the non-natural type diether sugar and the production of the final target product are described below.

The compound (3) is subjected to the condensation reaction with the compound (9) or (10) in the presence of silver perchlorate as an activator. Thus the target $\alpha$-glycoside, namely, the compound (11) or (12) can be respectively obtained. The compounds (9) or (10) is used in an amount of 1 mole to excess moles, generally about 4 to 8 moles per mole of the compound (3). The activator such as silver perchlorate is used in excess moles, preferably about 10 moles per mole of the compound (3) in view of improved yield. Usable as the activator for the condensation reaction are silver triflate, lithium perchlorate, trityl perchlorate, iodine-trityl perchlorate, silver carbonate, N-iodosuccinimide, methyl triflate, phenylselenyl triflate and dimethyl(methylthio)sulfonium triflate, in addition to the above-mentioned silver perchlorate. These compounds are used alone or as a mixture thereof. Examples of a solvent include acetonitrile, propionitrile, methylene chloride, benzene, toluene, dioxane and tetrahydrofuran. It is preferable to use acetonitrile as a solvent. The reaction proceeds at a temperature of $-20°$ to $30°$ C. The yield of the reaction products can be raised by adding molecular sieves. In this glycosylation reaction, a small amount of $\beta$-glycoside is sometimes formed as a side product depending on the reaction conditions. However this side product can be easily separated by silica gel thin layer chromatography, since it clearly differs from the $\alpha$-glycoside in Rf value. In the glycosylation reaction with the use of the compound (9) or (10), the glycosyl acceptor (i.e., a substance accepting the sugar component in the introduction of sugar chain) is not restricted to the compound (3) but the above-mentioned 9-dehydro-demycarosyl platenomycin is also usable. When 1-(2-pyridylthio) sugar is used as a glycosyl donor, the compound (3) gives a higher glycosylation yield.

The compound (11) or (12) is reacted with phosphine or a phosphite to obtain the compound (13) or (14) which is a compound of the formula (I) wherein $R^1$ is an oxygen atom, $R^2$ is a propionyl group, $R^3$ is a hydrogen atom, $R^4$ is a methyl group and $R^5$ is an ethyl or isoamyl group. Examples of the reducing agent for the N-oxide include phosphines such as triphenylphosphine and tri(n-butyl)phosphine and phosphites such as trimethyl phosphite and triethyl phosphite. Preferably, triphenylphosphine is used. The reducing agent is used in an amount of 1 mole to excess moles, preferably 15 to 20 moles per mole of the compound (11) or (12). The reaction is carried out at about $10°$ to $50°$ C. When methylene chloride is used as a solvent, the reaction is carried out at about $30°$ C. for 50 to 100 hours. Examples of a solvent include chloroform, methylene chloride, ethyl acetate, ether and benzene.

A compound of the formula (I) wherein $R^1$ is an oxygen atom, for example, the compound (13) or (14) can be easily converted into a compound wherein $R^1$ is a hydroxyl group and a hydrogen atom by the known biochemical method [Journal of Antibiotics, 32, 777 (1979)]. Furthermore, a compound of the formula (I) wherein $R^1$ is an oxygen atom, for example, the compound (13) or (14) and a derivative thereof formed by reducing at the 9-position can be easily converted into a compound wherein $R^2$ is a hydrogen atom by the known biochemical method (JP-A-54-28892).

The compounds of the formula (I) and (II) may be in the form of a pharmaceutically acceptable inorganic or organic acid salt. Examples of the salts include a salt of inorganic acid such as hydrochloric acid, sulfuric acid, nitric acid, phosphoric acid and a salt of organic acid such as acetic acid, stearic acid, malic acid and succinic acid.

Antibacterial activities of the compounds of formula (I) are shown in Table 1 in terms of minimum inhibitory concentration (MIC).

As Table 1 shows, the compounds (13), (14) and (39) to (44) of the present invention have antibacterial activities against gram-positive bacteria which are important from a clinical viewpoint. Among these compounds, the compounds (14) and (41) show excellent antibacterial activities exceeding that of miokamycin.

Minimum inhibitory concentration was determined by the agar plate dilution method. Test strains were subjected to seed culture using Sensitivity test broth (STB, Nissui Pharmaceutical) except that the strains belonging to the genus Streptococcus, Branhamella and Haemophilus were cultured on blood agar plate. A 5 $\mu l$ portion of cell suspension of the test strains having about $10^6$ CFU/ml was inoculated into Sensitivity disk agar (SDA, Nissui Pharmaceutical) supplemented with 5% horse blood and incubated at $37°$ C. for 20 hours. Then, MIC was measured.

TABLE 1

| Test strain | Antibacterial activity (MIC: μg/ml) | | | | | | | | |
|---|---|---|---|---|---|---|---|---|---|
| | Compound (13) | Compound (14) | Compound (39) | Compound (40) | Compound (41) | Compound (42) | Compound (43) | Compound (44) | Miokamycin |
| Sta. aureus 209P JC-1 | 3.13 | 0.20 | 3.13 | 0.78 | 0.20 | 0.78 | 0.39 | 0.20 | 0.20 |
| Sta. aureus M133 | 3.13 | 0.78 | 12.5 | 1.56 | 0.78 | 1.56 | 1.56 | 1.56 | 0.78 |
| Sta. aureus M126 | >100 | >100 | >100 | >100 | >100 | >100 | >100 | >100 | >100 |
| Sta. aureus MS15009/pMS99 | >100 | >100 | >100 | >100 | >100 | >100 | >100 | >100 | >100 |
| Sta. aureus MS15026 | >100 | >100 | >100 | >100 | >100 | >100 | >100 | >100 | >100 |
| Sta. aureus MS15009/pMS98 | 6.25 | 0.78 | 12.5 | 0.78 | 0.39 | 1.56 | 0.78 | 0.78 | 0.78 |
| Sta. aureus MS15027 | 6.25 | 0.78 | 12.5 | 1.56 | 0.78 | 1.56 | 1.56 | 1.56 | 0.78 |
| Sta. epidermidis ATCC 14990 | 12.5 | 0.78 | 25 | 3.13 | 1.56 | 1.56 | 1.56 | 3.13 | 0.78 |
| M. luteus ATCC 9341 | 0.78 | 0.10 | 0.39 | 0.10 | 0.05 | 0.10 | 0.05 | 0.10 | 0.10 |
| Ent. faecalis W-73 | 3.13 | 1.56 | 6.25 | 3.13 | 3.13 | 6.25 | 3.13 | 1.56 | 1.56 |
| E. coli NIHJ JC-2 | >100 | >100 | >100 | >100 | >100 | >100 | >100 | >100 | >100 |
| K. pneumoniae PC1602 | >100 | >100 | >100 | >100 | >100 | >100 | >100 | >100 | >100 |
| S. pneumoniae IP692 | 1.56 | 0.10 | 1.56 | 0.39 | 0.10 | 0.20 | 0.20 | 0.20 | 0.20 |
| S. pneumoniae Type 1 | 1.56 | 0.20 | 1.56 | 0.39 | 0.20 | 0.20 | 0.20 | 0.20 | 0.20 |
| S. Pyogenes Cook | 0.78 | 0.05 | 1.56 | 0.20 | 0.10 | 0.20 | 0.05 | 0.20 | 0.10 |
| B. catarrhalis W-0500 | 3.13 | 0.78 | 12.5 | 1.56 | 0.78 | 1.56 | 1.56 | 1.56 | 1.56 |
| B. catarrhalis W-0506 | 6.25 | 0.78 | 6.25 | 1.56 | 0.78 | 1.56 | 1.56 | 1.56 | 1.56 |
| H. influenza 9334 | 100 | 6.25 | | 12.5 | 6.25 | 12.5 | 12.5 | 6.25 | 6.25 |

The compounds (13) and (14) of the formula (I) obtained by the present invention are characterized by showing an antibacterial activity sustaining for a prolonged period of time in rat plasma. Changes in the antibacterial activities of miokamycin (MOM) and the compound (13) were measured in the following manner.

Each test compound and 50 μl of a methanol solution (10,000 γ) were added to 950 μl of thawed rat plasma and the resulting mixture was incubated at 37° C. A 20 μl portion of the mixture was sampled after 0, 1, 3, 6 and 24 hours and added to 980 μl of 0.05M phosphate buffer (pH 7.2). A 20 μl portion of the sample solution was used to measure antibacterial activity against M. luteus. Separately, the calibration curve was prepared by using a methanol solution containing each test compound. The starting activity of each compound in the plasma was referred to as 100%. The results are shown in FIG. 1.

Figure 2:
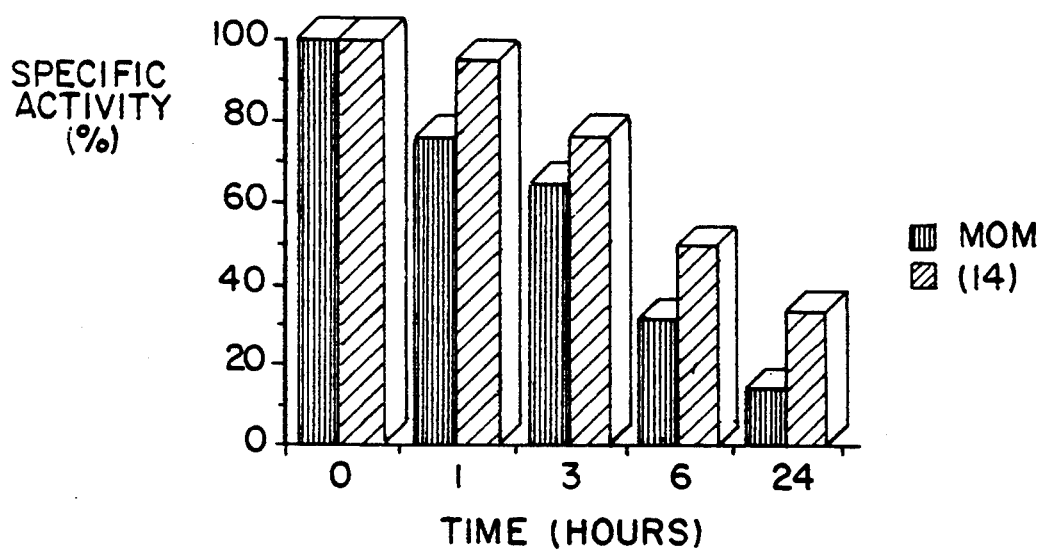
FIG. 2 shows changes in the antibacterial activities of miokamycin and the compound (14) against *M. luteus* in fresh-prepared rat plasma with the lapse of time.

Changes in the antibacterial activities of miokamycin and the compound (14) against M. luteus were measured in the same manner as described above except for using fresh rat plasma in place of thawed rat plasma. The fresh rat plasma was prepared by collecting 50 ml of blood from five rats, treating the blood with heparin and subjecting it to centrifugation to obtain plasma. The results are shown in FIG. 2.

In each of the tests with the use of the thawed rat plasma and the fresh one, the compounds (13) and (14) of the present invention having two ether bonds are hardly metabolized at the mycarose moiety and show a clearly lower degree of the decrease in the antibacterial activity in plasma, compared with miokamycin. According to the report of Shomura et al., the metabolic pattern of the deacylation of the mycarose moiety of miokamycin in human is almost similar to that in rat [Yakugaku Zasshi, 102(8), 781 (1982)]. It is, therefore, easily suggested that the compound of the present invention would show a sustained antibacterial activity for a prolonged period of time in human blood too.

It is furthermore suggested that the compounds of the formula (II) obtained by the present invention are valuable as a synthesis intermediate for producing the compound of the present invention since these compounds are excellent in stability and reaction selectivity and can be easily derived from natural substances.

The following examples are given to further illustrate the present invention in greater detail, but are not to be construed to limit the scope of the present invention.

EXAMPLE 1

Production of Compound (1) [Compound of Formula (II) wherein $R^7$ is an Ethylenedioxy Group, and $R^8$ is a Dimethylamino Group]

3.50 g of midecamycin $A_3$ was dissolved in 105 ml of anhydrous acetonitrile and 0.48 ml of ethylene glycol and 1.48 g of p-toluenesulfonic acid were successively added thereto. After reacting at room temperature for 1 hour, the reaction mixture was added dropwise to 1 L of a saturated aqueous solution of sodium hydrogencarbonate and extracted with 1 L and then 250 ml of chloroform. The chloroform layers were combined, dried over sodium sulfate anhydride and filtered. The filtrate was concentrated under reduced pressure and the residue thus obtained was purified by silica gel column chromatography [900 g, chloroform-methanol (15:1→7:1)]. Thus 2.61 g of the compound (1) was obtained.

Physicochemical Data of Compound (1)

(1) Color and form: colorless solid.
(2) Molecular formula: $C_{33}H_{53}NO_{12}$.
(3) Mass spectrum (EIMS): m/z 655 (M)+.
(4) Specific rotation: $[\alpha]_D^{15}+2.2°$ (C 1.0, $CH_3OH$).
(5) m.p.: 96°–99° C.
(6) $^1H$ NMR spectrum (400 MHz, $CDCl_3$) δ (ppm): 2.28 (dd, 2-H), 2.77 (dd, 2-H), 5.07 (br d, 3-H), 3.23 (dd, 4-H), 3.59 (s, 4-$OCH_3$), 4.09 (br d, 5-H), 1.41 (m, 6-H), 1.47 (ddd, 7-H), 1.59 (ddd, 7-H), 2.65 (m, 8-H), 6.31 (d, 10-H), 7.35 (ddd, 11-H), 6.19 (m, 12-H), 6.19 (m, 13-H), 2.21 (m, 14-H), 2.47 (br dt, 14-H), 4.91 (ddq, 15-H), 1.28 (d, 16-$H_3$), 1.76 (br dt, 17-H), 1.87 (ddd, 17-H), 4.77 (dd, 18-H), 1.19 (d, 19-$H_3$), 2.32 (dq, 3-$OCOCH_2CH_3$), 2.33 (dq, 3-$OCOCH_2CH_3$), 1.10 (t, 3-$OCOCH_2\underline{CH_3}$), 4.50 (d, 1'-H), 3.57 (dd, 2'-H), 2.37 (t, 3'-H), 3.05 (t, 4'-H), 3.30 (dq, 5'-H), 1.31 (d, 6'-$H_3$), 2.52 (s, 3'-$N(CH_3)_2$), 3.74, 3.89 (m, $OCH_2CH_2O$).

EXAMPLE 2

Production of Compound (2) [Compound of Formula (II) wherein $R^7$ is an Ethylenedioxy Group, and $R^8$ is a Dimethylamino Group N-oxide]

1.20 g of the compound (1) was dissolved in 24 ml of chloroform and 12 ml of a solution of m-chloroperbenzoic acid (348 mg) in chloroform was added thereto. After reacting at room temperature for 15 minutes, the reaction mixture was added dropwise to 500 ml of a saturated aqueous solution of sodium hydrogencarbonate and extracted with 500 ml and then 100 ml of chloroform. The chloroform layers were combined, dried over sodium sulfate anhydride and filtered. The filtrate was concentrated under reduced pressure and the residue thus obtained was purified by preparative TLC [development system: chloroform-methanol-conc. aqueous ammonia (100:10:1)]. Thus 1.07 g of the compound (2) was obtained.

Physicochemical Data of Compound (2)

(1) Color and form: colorless solid.
(2) Molecular formula: $C_{33}H_{53}NO_{13}$.
(3) Mass spectrum (FDMS): m/z 672 (M+H)+.
(4) Specific rotation: $[\alpha]_D^{15} +14°$ (C 1.0, $CH_3OH$)
(5) m.p.: 148°–151° C.
(6) $^1H$ NMR spectrum (400 MHz, $CDCl_3$) δ (ppm): 2.30 (dd, 2-H), 2.79 (dd, 2-H), 5.07 (br d, 3-H), 3.25 (dd, 4-H), 3.58 (s, 4-$OCH_3$), 4.15 (br d, 5-H), 1.48 (ddd, 7-H), 1.58 (ddd, 7-H), 2.67 (m, 8-H), 6.30 (d, 10-H), 7.35 (dd, 11-H), 6.19 (m, 12-H), 6.19 (m, 13-H), 2.21 (m, 14-H), 2.48 (br dt, 14-H), 4.95 (ddq, 15-H), 1.29 (d, 16-$H_3$), 4.70 (dd, 18-H), 1.20 (d, 19-$H_3$), 2.33 (dq, 3-$OCOCH_2CH_3$), 2.34 (dq, 3-$OCOCH_2CH_3$), 1.12 (t, 3-$OCOCH_2CH_3$), 4.54 (d, 1'-H), 3.49 (dd, 2'-H), 3.21 (t, 3'-H), 3.62 (t, 4'-H), 3.38 (dq, 5'-H), 1.38 (d, 6'-$H_3$), 3.26 (s, 3'-N($CH_3$)$_2$), 3.48 (s, 3'-N($CH_3$)$_2$), 3.75, 3.91 (m, $OCH_2C-H_2O$).

EXAMPLE 3

Production of Compound (3) [Compound of Formula (II) wherein $R^7$ is an Oxygen Atom, and $R^8$ is a Dimethylamino Group N-oxide]

1.05 g of the compound (2) was dissolved in 21 ml of acetonitrile and 21 ml of 1N hydrochloric acid was added thereto. After reacting at 30° C. for 15 hours, the reaction mixture was added dropwise to 200 ml of a saturated aqueous solution of sodium hydrogencarbonate and extracted with 200 ml and then 50 ml of chloroform. The chloroform layers were combined, dried over sodium sulfate anhydride and filtered. The filtrate was concentrated under reduced pressure and the residue thus obtained was purified by preparative TLC [development system: chloroform-methanol-conc. aqueous ammonia (100:10:1)]. Thus 785 mg of the compound (3) was obtained.

Physicochemical Data of Compound (3)

(1) Color and form: colorless solid.
(2) Molecular formula: $C_{31}H_{49}NO_{12}$.
(3) Mass spectrum (SIMS): m/z 628 (M+H)+.
(4) Specific rotation: $[\alpha]_D^{21} +43°$ (c 1.0, $CHCl_3$).
(5) m.p.: 158°–164° C.
(6) $^1H$ NMR spectrum (400 MHz, $CDCl_3$) δ (ppm): 2.29 (dd, 2-H), 2.77 (dd, 2-H), 5.09 (br dt, 3-H), 3.32 (dd, 4-H), 3.56 (s, 4-$OCH_3$), 3.88 (br d, 5-H), 1.87 (m, 6-H), 1.49 (ddd, 7-H), 1.57 (ddd, 7-H), 6.32 (d, 10-H), 7.37 (dd, 11-H), 6.21 (m, 12-H), 6.21 (m, 13-H), 2.23 (m, 14-H), 2.49 (br dt, 14-H), 4.90 (ddq, 15-H), 1.30 (d, 16-$H_3$), 2.58 (dd, 17-H), 2.70 (ddd, 17-H), 9.58 (br d, 18-H), 1.22 (d, 19-$H_3$), 2.42 (dq, 3-$OCOCH_2CH_3$), 2.53 (dq, 3-$OCOCH_2CH_3$), 1.14 (t, 3-$OCOCH_2CH_3$), 4.39 (d, 1'-H), 3.47 (dd, 2'-H), 3.20 (t, 3'-H), 3.56 (t, 4'-H), 3.40 (dq, 5'-H), 1.32 (d, 6'-$H_3$), 3.27 (s, 3'-N($CH_3$)$_2$), 3.44 (s, 3'-N($CH_3$)$_2$).

EXAMPLE 4

Production of Compound (4) [Ethyl 3-O-methyl-β-L-mycaroside (Ethyl β-L-cladinoside)]

50.0 g of erythromycin was dissolved in 102 ml of ethanol and 400 ml of anhydrous acetonitrile was added thereto. 23.5 g of p-toluenesulfonic acid was further added and the resulting mixture was allowed to react at room temperature for 1 hour. Then the reaction mixture was added dropwise to 6 L of a saturated aqueous solution of sodium hydrogencarbonate and extracted with 5 L and then 1.3 L of chloroform. The chloroform layers were combined, dried over sodium sulfate anhydride and filtered. The filtrate was concentrated under reduced pressure and the residue thus obtained was purified by silica gel column chromatography [1.25 kg, chloroform-methanol (30:1)] to thereby give 12.7 g of ethyl 3-O-methyl-L-mycaroside (ethyl L-cladinoside). This product was purified by silica gel column chromatography [1.25 kg, benzene-ethyl acetate (8:1→3:1)]. Thus 11.4 g of the compound (4) was obtained.

Physicochemical Data of Compound (4)

(1) Color and form: colorless oil.
(2) Molecular formula: $C_{10}H_{20}O_4$.
(3) Specific rotation: $[\alpha]_D^{19} +35°$ (c 1.0, $CHCl_3$).
(4) $^1H$ NMR spectrum (400 MHz, $CDCl_3$) δ (ppm): 4.57 (dd, 1-H), 1.40 (dd, 2-Hax), 2.24 (dd, 2-Heq), 2.97 (dd, 4-H), 3.59 (dq, 5-H), 1.30 (d, 6-$H_3$), 1.24 (s, 7-$H_3$), 3.50 (dq, 1-$OCH_2CH_3$), 3.93 (dq, 1-$OCH_2CH_3$), 1.22 (t, 1-$OCH_2CH_3$), 3.25 (s, 3-$OCH_3$), 2.09 (d, 4-OH).

EXAMPLE 5

Production of Compound (5) [Ethyl 4-O-ethyl-3-O-methyl-β-L-mycaroside (Ethyl 4-O-ethyl-β-L-cladinoside)]

2.85 g of the compound (4) was dissolved in 40 ml of anhydrous dimethylformamide and 2.22 g of 60% oily sodium hydride was added thereto, followed by stirring at room temperature. When bubbling was weakened, 4.5 ml of ethyl iodide was added to the mixture under cooling at 0° C. and then the mixture was stirred at room temperature for additional 70 minutes. The reaction mixture was concentrated under reduced pressure and the residue thus obtained was extracted with 300 ml of ethyl acetate. The ethyl acetate layer was washed successively with 300 ml of a 10% aqueous solution of potassium hydrogensulfate (once) and 300 ml of a saturated aqueous solution of sodium chloride (once). After drying over sodium sulfate anhydride, the product was filtered. The filtrate was concentrated under reduced pressure and the residue thus obtained was purified by silica gel column chromatography [60 g, benzene-ethyl acetate (7:1)] to thereby give 2.65 g of the compound (5).

Physicochemical Data of Compound (5)

(1) Color and form: colorless oil.
(2) Molecular formula: $C_{12}H_{24}O_4$.

(3) Mass spectrum (SIMS): m/z 233 (M+H)+.
(4) Specific rotation: $[\alpha]_D^{25}+19°$ (C 1.0, CHCl$_3$).
(5) $^1$H NMR spectrum (400 MHz, CDCl$_3$) δ (ppm): 4.66 (dd, 1-H), 1.39 (dd, 2-Hax), 2.15 (dd, 2-Heq), 2.78 (d, 4-H), 3.87 (dq, 5-H), 1.29 (d, 6-H$_3$), 1.26 (s, 7-H$_3$), 3.51 (dq, 1-OCH$_2$CH$_3$), 3.92 (dq, 1-OCH$_2$CH$_3$), 1.22 (t, 1-OCH$_2$CH$_3$), 3.29 (s, 3-OCH$_3$), 3.62 (dq, 4-OCH$_2$CH$_3$), 3.68 (dq, 4-OCH$_2$CH$_3$), 1.22 (t, 4-OCH$_2$CH$_3$).

EXAMPLE 6

Production of Compound (6) [Ethyl 4-O-isoamyl-3-O-methyl-β-L-mycaroside (Ethyl 4-O-isoamyl-β-L-cladinoside)]

6.25 g of the compound (4) was dissolved in 150 ml of anhydrous dimethylformamide and 6.20 g of 60% oily sodium hydride was added thereto, followed by stirring at room temperature. When bubbling was weakened, 30.3 g of isoamyl iodide was added and then the mixture was stirred at 60° C. for 15 hours. The reaction mixture was concentrated under reduced pressure and the residue thus obtained was extracted with 2 L of ethyl acetate. The ethyl acetate layer was washed successively with 2 L of a 10% aqueous solution of potassium hydrogensulfate (once) and 2 L of a saturated aqueous solution of sodium chloride (once). After drying over sodium sulfate anhydride, the product was filtered. The filtrate was concentrated under reduced pressure and the residue thus obtained was purified by silica gel column chromatography [750 g, benzene-ethyl acetate (10:1)] to thereby give 4.88 g of the compound (6).

Physicochemical Data of Compound (6)

(1) Color and Form: colorless oil.
(2) Molecular formula: C$_{15}$H$_{30}$O$_4$.
(3) Mass spectrum (SIMS): m/z 275 (M+H)+.
(4) Specific rotation: $[\alpha]_D^{18}+16°$ (C 1.0, CHCl$_3$).
(5) $^1$H NMR spectrum (400 MHz, CDCl$_3$) δ (ppm): 4.69 (dd, 1-H), 1.42 (dd, 2-Hax), 2.14 (dd, 2-Heq), 2.78 (d, 4-H), 3.88 (dq, 5-H), 1.31 (d, 6-H$_3$), 1.28 (s, 7-H$_3$), 3.52 (dq, 1-OCH$_2$CH$_3$), 3.93 (dq, 1-OCH$_2$CH$_3$), 1.23 (t, 1-OCH$_2$CH$_3$), 3.31 (s, 3-OCH$_3$), 3.59 (dt, 4-OCH$_2$CH$_2$CH(CH$_3$)$_2$), 3.65 (ddd, 4-OCH$_2$CH$_2$CH(CH$_3$)$_2$), 1.52 (m, 4-OCH$_2$CH$_2$CH(CH$_3$)$_2$), 1.73 (m, 4-OCH$_2$CH$_2$CH(CH$_3$)$_2$), 0.91 (d, 4-OCH$_2$CH$_2$CH(CH$_3$)$_2$).

EXAMPLE 7

Production of Compound (9)
[1-deoxy-4-O-ethyl-3-O-methyl-1-(2-pyridylthio)-L-mycaroside
[1-deoxy-4-O-ethyl-1-(2-pyridylthio)-L-cladinoside)]

2.65 g of the compound (5) was dissolved in 40 ml of 1,4-dioxane and 40 ml of 1N hydrochloric acid was added thereto, followed by stirring at 30° C. for 15 hours. Under cooling at 0° C., the mixture was neutralized by adding 40 ml of a 1N aqueous solution of sodium hydroxide. After concentrating under reduced pressure, the residue thus obtained was extracted with 260 ml of chloroform. The chloroform layer was washed with 260 ml of a saturated aqueous solution of sodium chloride once, dried over sodium sulfate anhydride and then filtered. The filtrate was concentrated under reduced pressure to thereby give 2.17 g of the compound (7) [4-O-ethyl-3-O-methyl-L-mycarose (4-O-ethyl-L-cladinose)] as a colorless, oily product. 1.97 g of the compound (7) was dissolved in 26 ml of anhydrous methylene chloride and cooled to 0° C. On the other hand, 2.94 g of aldolithiol-2 was dissolved in 32 ml of anhydrous methylene chloride and 4.4 ml of tri(n-butyl)phosphine was added thereto. After cooling to 0° C., the mixture was added to the above-mentioned solution. Then the obtained mixture was allowed to react under an argon atmosphere at room temperature for 4 hours and then concentrated under reduced pressure. The residue thus obtained was purified by silica gel column chromatography [500 g, chloroform→chloroform-ethyl acetate (10:1)]. Thus 1.74 g of the compound (9) was obtained.

Physicochemical Data of Compound (9)

(1) Color and form: colorless oil.
(2) Molecular formula: C$_{15}$H$_{23}$NO$_3$S.
(3) Mass spectrum (EIMS): m/z 297 (M)+.
(4) Specific rotation: $[\alpha]_D^{24}-114°$ (c 1.0, CHCl$_3$) (α:β≈2:3).
(5) $^1$H NMR spectrum (400 MHz, CDCl$_3$) of compound (9) α-thioglycoside δ (ppm): 6.32 (br d, 1-H), 2.06 (dd, 2-Hax), 2.41 (br d, 2-Heq), 2.83 (d, 4-H), 4.38 (dq, 5-H), 1.26 (d, 6-H$_3$), 1.31 (s, 7-H$_3$), 3.35 (s, 3-OCH$_3$), 1.24 (t, 4-OCH$_2$CH$_3$), 7.28 (dt, 3'-H), 7.49 (dt, 4'-H), 6.99 (ddd, 5'-H), 8.45 (ddd, 6'-H).
(6) $^1$H NMR spectrum (400 MHz, CDCl$_3$) of compound (9) β-thioglycoside δ (ppm): 5.58 (dd, 1-H), 1.72 (dd, 2-Hax), 2.36 (dd, 2-Heq), 2.84 (d, 4-H), 4.03 (dq, 5-H), 1.31 (d, 6-H$_3$), 1.31 (s, 7-H$_3$), 3.32 (s, 3-OCH$_3$), 1.24 (t, 4-OCH$_2$CH$_3$), 7.33 (dt, 3'-H), 7.55 (dt, 4'-H), 7.03 (ddd, 5'-H), 8.44 (ddd, 6'-H).

EXAMPLE 8

Production of Compound (10)
[4-O-isoamyl-1-deoxy-3-O-methyl-1-(2-pyridylthio)-L-mycaroside
[4-O-isoamyl-1-deoxy-1-(2-pyridylthio)-L-cladinoside)]

4.56 of the compound (6) was dissolved in 80 ml of 1,4-dioxane and 80 ml of 1N hydrochloric acid was added thereto, followed by stirring at 30° C. for 15 hours. Under cooling at 0° C., the mixture was neutralized by adding 80 ml of a 1N aqueous solution of sodium hydroxide. After concentrating under reduced pressure, the residue thus obtained was extracted with 400 ml of chloroform. The chloroform layer was washed with 400 ml of a saturated aqueous solution of sodium chloride once, dried over sodium sulfate anhydride and then filtered. The filtrate was concentrated under reduced pressure to thereby give 4.09 g of the compound (8) [4-O-isoamyl-3-O-methyl-L-mycarose (4-O-isoamyl-L-cladinose)] as a colorless, oily product. 4.08 g of the compound (8) was dissolved in 74 ml of anhydrous methylene chloride and cooled to 0° C. On the other hand, 8.26 g of aldolithiol-2 was dissolved in 89 ml of anhydrous methylene chloride and 12.4 ml of tri(n-butyl)phosphine was added thereto. After cooling to 0° C., the mixture was added to the above-mentioned solution. Then the obtained mixture was allowed to react under an argon atmosphere at room temperature for 4 hours and then concentrated under reduced pressure. The residue thus obtained was purified by silica gel column chromatography [1 kg, chloroform→chloroform-ethyl acetate (10:1)]. Thus 3.51 g of the compound (10) was obtained. Further, the α-thioglycoside and β-thioglycoside of the compound (10) could be separated from each other with the use of preparative TLC [chloroform-ethyl acetate (10:1)].

Physicochemical Data of Compound (10)
α-thioglycoside (1) Color and form: colorless needles.
(2) Molecular formula: $C_{18}H_{29}NO_3S$.
(3) Mass spectrum (FDMS): m/z 339 (M)+.
(4) Specific rotation: $[\alpha]_D^{18} -311°$ (c 1.0, $CHCl_3$)
(5) m.p.: 76° C.
(6) $^1H$ NMR spectrum (400 MHz, $CDCl_3$) δ (ppm): 6.33 (br d, 1-H), 2.07 (dd, 2-Hax), 2.38 (br d, 2-Heq), 2.82 (d, 4-H), 4.37 (dq, 5-H), 1.26 (d, 6-$H_3$), 1.31 (s, 7-$H_3$), 3.35 (s, 3-$OCH_3$), 3.60 (dt, 4-$OCH_2CH_2CH(CH_3)_2$), 3.67 (ddd, 4-$OCH_2CH_2CH(CH_3)_2$), 1.52 (m, 4-$OCH_2CH_2CH(CH_3)_2$), 1.73 (m, 4-$OCH_2CH_2CH(CH_3)_2$), 0.90 (d, 4-$OCH_2CH_2CH(CH_3)_2$), 7.27 (dt, 3'-H), 7.49 (dt, 4'-H), 6.98 (ddd, 5'-H), 8.45 (ddd, 6'-H).

Physicochemical Data of Compound (10)
β-thioglycoside (1) Color and form: colorless oil.
(2) Molecular formula: $C_{18}H_{29}NO_3S$.
(3) Mass spectrum (FDMS): m/z 339 (M)+.
(4) Specific rotation: $[\alpha]_D^{18} +27°$ (c 1.0, $CHCl_3$)
(5) $^1H$ NMR spectrum (400 MHz, $CDCl_3$) δ (ppm): 5.59 (dd, 1-H), 1.73 (dd, 2-Hax), 2.33 (dd, 2-Heq), 2.83 (d, 4-H), 4.02 (dq, 5-H), 1.30 (d, 6-$H_3$), 1.31 (s, 7-$H_3$), 3.32 (s, 3-$OCH_3$), 3.59 (ddd, 4-$OCH_2CH_2CH(CH_3)_2$), 3.65 (ddd, 4-$OCH_2CH_2CH(CH_3)_2$), 1.51 (m, 4-$OCH_2CH_2CH(CH_3)_2$), 1.71 (m, 4-$OCH_2CH_2CH(CH_3)_2$), 0.90 (d, 4-$OCH_2CH_2CH(CH_3)_2$), 7.32 (dt, 3'-H), 7.55 (ddd, 4'-H), 7.03 (ddd, 5'-H), 8.43 (ddd, 6'-H).

EXAMPLE 9

Production of Compound (13) [Compound of Formula (I) wherein $R^1$ is an Oxygen Atom, $R^2$ is a Propionyl Group, $R^3$ is a Hydrogen Atom, $R^4$ is a Methyl Group and $R^5$ is an Ethyl Group]

489 mg of the compound (3) was dissolved in 30 ml of anhydrous acetonitrile. The solution thus obtained was added to 1.27 g of the compound (9) to thereby give a homogeneous solution. Separately, 1.05 g of silver perchlorate was dissolved in 32 ml of anhydrous acetonitrile and then added to the above-mentioned solution. After stirring in the dark under an argon atmosphere for 15 hours, the reaction mixture was added dropwise to 600 ml a saturated aqueous solution of sodium hydrogencarbonate and extracted with 600 ml and then 150 ml of chloroform. The chloroform layers were combined, dried over sodium sulfate anhydride and filtered. Then the filtrate was concentrated under reduced pressure and the residue thus obtained was purified by preparative TLC [development system: chloroform-methanol (10:1)] to thereby give 20.6 mg of the compound (11) [9-dehydro-4''-O-ethyl-3''-O-methyl-3-O-propionylleucomycin V N-oxide]. Further, 306 mg of the compound (3) was collected simultaneously. 20.6 mg of the compound (11) and 36 mg of triphenylphosphine were dissolved in 1.3 ml of anhydrous methylene chloride and allowed to react at 30° C. for 15 hours. The reaction mixture was concentrated under reduced pressure and the residue thus obtained was purified by preparative TLC [development system: hexane-acetone (1:1)]. Thus 7.2 mg of the compound (13) was obtained.

Physicochemical Data of Compound (13)

(1) Color and form: colorless solid.
(2) Molecular formula: $C_{41}H_{67}NO_{14}$.
(3) Mass spectrum (SIMS): m/z 798 (M+H)+.
(4) Specific rotation: $[\alpha]_D^{20} -22°$ (c 0.7, $CH_3OH$)
(5) m.p.: 104°–107° C.
(6) $^1H$ NMR spectrum (400 MHz, $CDCl_3$) δ (ppm): 2.26 (br d, 2-H), 2.78 (dd, 2-H), 5.09 (br dt, 3-H), 3.29 (dd, 4-H), 3.60 (s, 4-$OCH_3$), 3.89 (br d, 5-H), 1.78 (m, 6-H), 1.49 (ddd, 7-H), 1.64 (ddd, 7-H), 6.34 (d, 10-H), 7.37 (dd, 11-H), 6.21 (m, 12-H), 6.21 (m, 13-H), 4.85 (ddq, 15-H), 1.28 (d, 16-$H_3$), 2.75 (br dd, 17-H), 9.54 (br s, 18-H), 1.20 (d, 19-$H_3$), 2.43 (dq, 3-$OCOCH_2CH_3$), 2.58 (dq, 3-$OCOCH_2CH_3$), 1.14 (t, 3-$OCOCH_2CH_3$), 4.51 (d, 1'-H), 3.14 (dd, 2'-H), 2.39 (t, 3'-H), 3.47 (t, 4'-H), 3.27 (dq, 5'-H), 1.15 (d, 6'-$H_3$), 2.56 (s, 3'-$N(CH_3)_2$), 4.89 (d, 1''-H), 1.55 (dd, 2''-Hax), 2.24 (d, 2''-Heq), 2.78 (d, 4''-H), 4.43 (dq, 5''-H), 1.23 (d, 6''-$H_3$), 1.24 (s, 7''-$H_3$), 3.25 (s, 3''-$OCH_3$), 3.65 (dq, 4''-$OCH_2CH_3$), 3.70 (dq, 4''-$OCH_2CH_3$), 1.23 (t, 4''-$OCH_2CH_3$).

EXAMPLE 10

Production of Compound (14) [Compound of Formula (I) wherein $R^1$ is an Oxygen Atom, $R^2$ is a Propionyl Group, $R^3$ is a Hydrogen Atom, $R^4$ is a Methyl Group and $R^5$ is an Isoamyl Group]

1.07 g of the compound (3) was dissolved in 65 ml of anhydrous acetonitrile. The solution thus obtained was added to 3.17 g of the compound (10) to thereby give a homogeneous solution. Separately, 2.30 g of silver perchlorate was dissolved in 70 ml of anhydrous acetonitrile and then added to the above-mentioned solution. After stirring in the dark under an argon atmosphere for 15 hours, the reaction mixture was added dropwise to 1.3 L of a saturated aqueous solution of sodium hydrogencarbonate and extracted with 1.3 L and then 350 ml of chloroform. The chloroform layers were combined, dried over sodium sulfate anhydride and filtered. Then the filtrate was concentrated under reduced pressure and the residue thus obtained was purified by preparative TLC [development system: chloroform-methanol (10:1)] to thereby give 30.7 mg of the compound (12) [4''-O-isoamyl-9-dehydro-3''-O-methyl-3-O-propionylleucomycin V N-oxide]. Further, 538 mg of the compound (3) was collected simultaneously. 30.7 mg of the compound (12) and 50 mg of triphenylphosphine were dissolved in 1.2 ml of anhydrous methylene chloride and allowed to react at 30° C. for 15 hours. The reaction mixture was concentrated under reduced pressure and the residue thus obtained was purified by preparative TLC [development system: hexane-acetone (1:1)]. Thus 10.5 mg of the compound (14) was obtained.

Physicochemical Data of Compound (14)

(1) Color and form: colorless solid.
(2) Molecular formula: $C_{44}H_{73}NO_{14}$.
(3) Mass spectrum (SIMS): m/z 840 (M+H)+.
(4) Specific rotation: $[\alpha]_D^{14} -23°$ (c 1.0, $CH_3OH$)
(5) m.p.: 89°–94° C.
(6) $^1H$ NMR spectrum (400 MHz, $CDCl_3$) δ (ppm): 2.25 (br d, 2-H), 2.78 (dd, 2-H), 5.09 (br dt, 3-H), 3.29 (dd, 4-H), 3.60 (s, 4-$OCH_3$), 3.89 (br dd, 5-H), 1.78 (m, 6-H), 1.65 (ddd, 7-H), 6.34 (d, 10-H), 7.37 (dd, 11-H), 6.22 (m, 12-H), 6.22 (m, 13-H), 4.84 (ddq, 15-H), 1.28 (d, 16-$H_3$), 2.76 (br dd, 17-H), 9.54 (br s, 18-H), 1.19 (d, 19-H$_3$), 2.41 (q, 3-OCOC$\underline{H}_2$CH$_3$), 2.45 (q, 3-OCOC$\underline{H}_2$CH$_3$), 1.14 (t, 3-OCOCH$_2$C$\underline{H}_3$), 4.50 (d, 1'-H), 3.14 (dd, 2'-H), 2.39 (t, 3'-H), 3.46 (t, 4'-H), 3.27 (dq, 5'-H), 1.15 (d, 6'-H$_3$), 2.56 (s, 3'-N(CH$_3$)$_2$), 4,88 (d, 1"-H), 1.56 (dd, 2"-Hax), 2.22 (d, 2"-Heq), 2.77 (d, 4"-H), 4.42 (dq, 5"-H), 1.23 (d, 6"-H$_3$), 1.24 (s, 7"-H$_3$), 3.25 (s, 3"-OCH$_3$), 3,59 (dt, 4"-OC$\underline{H}_2$CH$_2$CH(CH$_3$)$_2$), 3.64 (dt, 4"-OC$\underline{H}_2$CH$_2$CH(CH$_3$)$_2$), 1.51 (m, 4"-OCH$_2$C$\underline{H}_2$CH(CH$_3$)$_2$), 1.69 (m, 4"-OCH$_2$C$\underline{H}_2$CH(CH$_3$)$_2$), 0.89 (d, 4"-OCH$_2$CH$_2$C$\underline{H}$(CH$_3$)$_2$).

EXAMPLE 11

Production of Compound (15) [Ethyl 4-O-allyl-3-O-methyl-β-L-mycaroside (Ethyl 4-O-allyl-β-L-cladinoside)]

2.80 g of the compound (4) was dissolved in 67 ml of anhydrous dimethylformamide and 2.74 g of 60% oily sodium hydride was added thereto, followed by stirring at room temperature. When bubbling was weakened, 9.21 g of allyl iodide was added under cooling at 0° C. and then the mixture was stirred at room temperature for 1 hour. The reaction mixture was concentrated under reduced pressure and the residue thus obtained was extracted with 670 ml of ethyl acetate. The ethyl acetate layer was washed successively with 500 ml of a 5% aqueous solution of potassium hydrogensulfate (once), 500 ml of a saturated aqueous solution of sodium hydrogensulfate (once) and 500 ml of a saturated aqueous solution of sodium chloride (once). After drying over sodium sulfate anhydride, the product was filtered. The filtrate was concentrated under reduced pressure and the residue thus obtained was purified by silica gel column chromatography [280 g, benzene-ethyl acetate (10:1→6:1)] to thereby give 3.00 g of the compound (15).

Physicochemical Data of Compound (15)

(1) Color and form: colorless oil.
(2) Molecular formula: C$_{13}$H$_{24}$O$_4$.
(3) Specific rotation: [α]$_D^{21}$+19° (C 1.0, CHCl$_3$).
(4) $^1$H NMR spectrum (400 MHz, CDCl$_3$) δ (ppm): 4.67 (dd, 1-H), 1.40 (dd, 2-Hax), 2.14 (dd, 2-Heq), 2.86 (d, 4-H), 3.90 (dq, 5-H), 1.30 (d, 6-H$_3$), 1.26 (s, 7-H$_3$), 3.51 (dq, 1-OC$\underline{H}_2$CH$_3$), 3.92 (dq, 1-OC$\underline{H}_2$CH$_3$), 1.22 (t, 1-OCH$_2$C$\underline{H}_3$), 3.29 (s, 3-OCH$_3$), 4.08 (br dd, 4-OC$\underline{H}_2$CHCH$_2$), 4.18 (br dd, 4-OC$\underline{H}_2$CHCH$_2$), 5.94 (ddt, 4-OCH$_2$C$\underline{H}$CH$_2$), 5.16 (br d, 4-OCH$_2$CHC$\underline{H}_2$), 5.24 (br d, 4-OCH$_2$CHC$\underline{H}_2$).

EXAMPLE 12

Production of Compound (16) [Ethyl 3-O-methyl-4-O-(3-methyl-2-butenyl)-β-L-mycaroside (Ethyl 4-O-(3-methyl-2-butenyl)-β-L-cladinoside)]

2.79 g of the compound (4) was dissolved in 67 ml of anhydrous dimethylformamide and 2.73 g of 60% oily sodium hydride was added thereto, followed by stirring at room temperature. When bubbling was weakened, 8.11 g of 1-bromo-3-methyl-2-butene was added under cooling at 0° C. and then the mixture was stirred at room temperature for 80 minutes. The reaction mixture was concentrated under reduced pressure and the residue thus obtained was extracted with 670 ml of ethyl acetate. The ethyl acetate layer was washed successively with 500 ml of a 5% aqueous solution of potassium hydrogensulfate (once), 500 ml of a saturated aqueous solution of sodium hydrogensulfate (once) and 500 ml of a saturated aqueous solution of sodium chloride (once). After drying over sodium sulfate anhydride, the product was filtered. The filtrate was concentrated under reduced pressure and the residue thus obtained was purified by silica gel column chromatography [280 g, benzene-ethyl acetate (10:1→6:1)] to thereby give 3.56 g of the compound (16).

Physicochemical Data of Compound (16)

(1) Color and form: colorless oil.
(2) Molecular formula: C$_{15}$H$_{28}$O$_4$.
(3) Mass spectrum (EIMS): m/z 272 (M)$^+$.
(4) Specific rotation: [α]$_D^{25}$+17° (c 1.0, CHCl$_3$).
(5) $^1$H NMR spectrum (400 MHz, CDCl$_3$) δ (ppm): 4.66 (dd, 1-H), 1.39 (dd, 2-Hax), 2.14 (dd, 2-Heq), 2.82 (d, 4-H), 3.89 (dq, 5-H), 1.30 (d, 6-H$_3$), 1.26 (s, 7-H$_3$), 3.51 (dq, 1-OC$\underline{H}_2$CH$_3$), 3.91 (dq, 1-OC$\underline{H}_2$CH$_3$), 1.21 (t, 1-OCH$_2$C$\underline{H}_3$), 3.28 (s, 3-OCH$_3$), 4.09 (br dd, 4-OC$\underline{H}_2$CHC(CH$_3$)$_2$), 4.13 (br dd, 4-OC$\underline{H}_2$CHC(CH$_3$)$_2$), 5.37 (br t, 4-OCH$_2$C$\underline{H}$C(CH$_3$)$_2$), 1.66 (br s, 4-OCH$_2$CHC(C$\underline{H}_3$)$_2$), 1.73 (br s, 4-OCH$_2$CHC(C$\underline{H}_3$)$_2$).

EXAMPLE 13

Production of Compound (17) [Ethyl 4-O-butyl-3-O-methyl-β-L-mycaroside (Ethyl 4-O-butyl-β-L-cladinoside)]

2.90 g of the compound (4) was dissolved in 70 ml of anhydrous dimethylformamide and 2.84 g of 60% oily sodium hydride was added thereto, followed by stirring at room temperature. When bubbling was weakened, 7.78 g of butyl bromide was added under cooling at 0° C. and then the mixture was stirred at room temperature for 2 hours. The reaction mixture was concentrated under reduced pressure and the residue thus obtained was extracted with 700 ml of ethyl acetate. The ethyl acetate layer was washed successively with 500 ml of a 5% aqueous solution of potassium hydrogensulfate (once), 500 ml of a saturated aqueous solution of sodium hydrogensulfate (once) and 500 ml of a saturated aqueous solution of sodium chloride (once). After drying over sodium sulfate anhydride, the product was filtered. The filtrate was concentrated under reduced pressure and the residue thus obtained was purified by silica gel column chromatography [280 g, benzene-ethyl acetate (10:1→6:1)] to thereby give 3.49 g of the compound (17).

Physicochemical Data of Compound (17)

(1) Color and form: colorless oil.
(2) Molecular formula: C$_{14}$H$_{28}$O$_4$.
(3) Specific rotation: [α]$_D^{25}$+17° (C 1.0, CHCl$_3$).
(4) $^1$H NMR spectrum (400 MHz, CDCl$_3$) δ (ppm): 4.66 (dd, 1-H), 1.40 (dd, 2-Hax), 2.13 (dd, 2-Heq), 2.76 (d, 4-H), 3.87 (dq, 5-H), 1.29 (d, 6-H$_3$), 1.26 (s, 7-H$_3$), 3.51 (dq, 1-OC$\underline{H}_2$CH$_3$), 3.91 (dq, 1-OC$\underline{H}_2$CH$_3$), 1.22 (t, 1-OCH$_2$C$\underline{H}_3$), 3.29 (s, 3-OCH$_3$), 3.54 (dt, 4-OC$\underline{H}_2$CH$_2$CH$_2$CH$_3$), 3.61 (dt, 4-OC$\underline{H}_2$CH$_2$CH$_2$CH$_3$), 0.91 (t, 4-OCH$_2$CH$_2$CH$_2$C$\underline{H}_3$).

EXAMPLE 14

Production of Compound (18) [Ethyl 4-O-hexyl-3-O-methyl-β-L-mycaroside (Ethyl 4-O-hexyl-β-L-cladinoside)]

2.80 g of the compound (4) was dissolved in 67 ml of anhydrous dimethylformamide and 2.74 g of 60% oily sodium hydride was added thereto, followed by stirring at room temperature. When bubbling was weakened, 11.6 g of hexyl iodide was added under cooling at 0° C. and then the mixture was stirred at room temperature for 1 hour and then heated to 50° C. overnight. The reaction mixture was concentrated under reduced pressure and the residue thus obtained was extracted with 670 ml of ethyl acetate. The ethyl acetate layer was washed successively with 500 ml of a 5% aqueous solution of potassium hydrogensulfate (once), 500 ml of a saturated aqueous solution of sodium hydrogensulfate (once) and 500 ml of a saturated aqueous solution of sodium chloride (once). After drying over sodium sulfate anhydride, the product was filtered. The filtrate was concentrated under reduced pressure and the residue thus obtained was purified by silica gel column chromatography [280 g, toluene-ethyl acetate (10:1→6:1)] to thereby give 4.21 g of the compound (18).

Physical Data of Compound (18)

(1) Color and form: colorless oil.
(2) Molecular formula: $C_{16}H_{32}O_4$.
(3) Mass spectrum (EIMS): m/z 288 (M)+.
(4) Specific rotation: $[\alpha]_D^{21} +12°$ (c 0.5, CHCl$_3$).
(5) $^1$H NMR spectrum (400 MHz, CDCl$_3$) δ (ppm): 4.66 (dd, 1-H), 1.39 (dd, 2-Hax), 2.13 (dd, 2-Heq), 2.76 (d, 4-H), 3.87 (dq, 5-H), 1.29 (d, 6-H$_3$), 1.26 (s, 7-H$_3$), 3.50 (dq, 1-OC$\underline{H}_2$CH$_3$), 3.91 (dq, 1-OC$\underline{H}_2$CH$_3$), 1.22 (t, 1-OCH$_2$C$\underline{H}_3$), 3.29 (s, 3-OCH$_3$), 3.53 (dt, 4-OC$\underline{H}_2$CH$_2$CH$_2$CH$_2$CH$_2$CH$_3$), 3.60 (dt, 4-OC$\underline{H}_2$CH$_2$CH$_2$CH$_2$CH$_2$CH$_3$), 0.88 (t, 4-OCH$_2$CH$_2$CH$_2$CH$_2$CH$_2$C$\underline{H}_3$).

EXAMPLE 15

Production of Compound (19) [Ethyl 3-O-methyl-4-O-(4-methyl-pentyl)-β-L-mycaroside (Ethyl 4-O-(4-methylpentyl)-β-L-cladinoside)]

2.80 g of the compound (4) was dissolved in 67 ml of anhydrous dimethylformamide and 2.19 g of 60% oily sodium hydride was added thereto, followed by stirring at room temperature. When bubbling was weakened, 6.78 g of 1-bromo-4-methylpentane was added under cooling at 0° C. and then the mixture was stirred at room temperature for 90 minutes. The reaction mixture was concentrated under reduced pressure and the residue thus obtained was extracted with 670 ml of ethyl acetate. The ethyl acetate layer was washed successively with 500 ml of a 5% aqueous solution of potassium hydrogensulfate (once), 500 ml of a saturated aqueous solution of sodium hydrogensulfate (once) and 500 ml of a saturated aqueous solution of sodium chloride (once). After drying over sodium sulfate anhydride, the product was filtered. The filtrate was concentrated under reduced pressure and the residue thus obtained was purified by silica gel column chromatography [280 g, toluene-ethyl acetate (10:1→6:1)] to thereby give 3.44 g of the compound (19).

Physicochemical Data of Compound (19)

(1) Color and form: colorless oil.
(2) Molecular formula: $C_{16}H_{32}O_4$.
(3) Mass spectrum (SIMS): m/z 289 (M+H)+.
(4) Specific rotation: $[\alpha]_D^{24} +10°$ (c 1.0, CHCl$_3$).
(5) $^1$H NMR spectrum (400 MHz, CDCl$_3$) δ (ppm): 4.67 (dd, 1-H), 1.40 (dd, 2-Hax), 2.13 (dd, 2-Heq), 2.76 (d, 4-H), 3.87 (dq, 5-H), 1.29 (d, 6-H$_3$), 1.26 (s, 7-H$_3$), 3.51 (dq, 1-OC$\underline{H}_2$CH$_3$), 3.91 (dq, 1-OC$\underline{H}_2$CH$_3$), 1.22 (t, 1-OCH$_2$C$\underline{H}_3$), 3.29 (s, 3-OCH$_3$), 3.52 (dt, 4-OC$\underline{H}_2$CH$_2$CH$_2$CH(CH$_3$)$_2$), 3.59 (dt, 4-OC$\underline{H}_2$CH$_2$CH$_2$CH(CH$_3$)$_2$), 0.88 (d, 4-OCH$_2$CH$_2$CH$_2$CH(C$\underline{H}_3$)$_2$).

EXAMPLE 16

Production of Compound (20) [Ethyl 4-O-benzyl-3-O-methyl-β-L-mycaroside (Ethyl 4-O-benzyl-β-L-cladinoside)]

2.80 g of the compound (4) was dissolved in 67 ml of anhydrous dimethylformamide and 2.74 g of 60% oily sodium hydride was added thereto, followed by stirring at room temperature. When bubbling was weakened, 9.37 g of benzyl bromide was added under cooling at 0° C. and then the mixture was stirred at room temperature for 2 hours. The reaction mixture was concentrated under reduced pressure and the residue thus obtained was extracted with 670 ml of ethyl acetate. The ethyl acetate layer was washed successively with 500 ml of a 5% aqueous solution of potassium hydrogensulfate (once), 500 ml of a saturated aqueous solution of sodium hydrogensulfate (once) and 500 ml of a saturated aqueous solution of sodium chloride (once). After drying over sodium sulfate anhydride, the product was filtered. The filtrate was concentrated under reduced pressure and the residue thus obtained was purified by silica gel column chromatography [280 g, toluene→toluene-ethyl acetate (5:1)] to thereby give 3.70 g of the compound (20).

Physicochemical Data of Compound (20)

(1) Color and form: colorless needles.
(2) Molecular formula: $C_{17}H_{26}O_4$.
(3) Specific rotation: $[\alpha]_D^{28} +28°$ (c 1.0, CHCl$_3$).
(4) m.p.: 51°–55° C.
(5) $^1$H NMR spectrum (400 MHz, CDCl$_3$) δ (ppm): 4.69 (dd, 1-H), 1.41 (dd, 2-Hax), 2.13 (dd, 2-Heq), 2.99 (d, 4-H), 3.95 (dq, 5-H), 1.31 (d, 6-H$_3$), 1.20 (s, 7-H$_3$), 3.51 (dq, 1-OC$\underline{H}_2$CH$_3$), 3.92 (dq, 1-OC$\underline{H}_2$CH$_3$), 1.22 (t, 1-OCH$_2$C$\underline{H}_3$), 3.30 (s, 3-OCH$_3$), 4.60 (d, 4-OC$\underline{H}_2$C$_6$H$_5$), 4.69 (d, 4-OC$\underline{H}_2$C$_6$H$_5$), 7.34 (m, 4-OCH$_2$C$_6$$\underline{H}_5$).

EXAMPLE 17

Production of Compound (39) [Compound of Formula (I) wherein R$^1$ is an Oxygen Atom, R$^2$ is a Propionyl Group, R$^3$ is a Hydrogen Atom, R$^4$ is a Methyl Group and R$^5$ is an Allyl Group]

2.98 g of the compound (15) was dissolved in 60 ml of 1,4-dioxane. Then 60 ml of 1N hydrochloric acid was added thereto and the resulting mixture was allowed to react at room temperature over two days. 150 ml of a saturated aqueous solution of sodium hydrogencarbonate was slowly added to the reaction mixture and then the resulting mixture was extracted with 120 ml of methylene chloride. The aqueous layer was further extracted with 120 ml of methylene chloride again. The methylene chloride layers were combined and washed with 100 ml portions of a saturated aqueous solution of sodium chloride twice. The methylene chloride layer was dried over sodium sulfate anhydride and filtered. After concentrating the filtrate under reduced pressure, 2.83 g of a crude compound (21) [4-O-allyl-3-O-methyl-L-mycarose (4-O-allyl-L-cladinoside)] was obtained. 2.83 g of this crude compound (21) was dissolved in 40 ml of anhydrous methylene chloride and cooled to 0° C. Separately, 4.62 g of aldolithiol-2 was dissolved in 40 ml of the same solvent. After adding 6.5 ml of tri(n-butyl)phosphine, the mixture was cooled to the same temperature and then added dropwise to the above-mentioned solution. After allowing to react for one day at room temperature, the reaction mixture was concentrated under reduced pressure. The residue thus obtained was purified by silica gel column chromatography [500 g, chloroform-ethyl acetate (100:1)] to thereby give 3.00 g of a crude compound (27) [4-O-allyl-1-deoxy-3-O-methyl-1-(2-pyridylthio)-L-mycaroside (4-O-allyl-1-deoxy-1-(2-pyridylthio)-L-cladinose)]. 2.00 g of this crude compound (27), which had been highly dried, and 676 mg of the compound (3) were dissolved in 18 ml of anhydrous acetonitrile. Then 6.0 g of an activated molecular sieve 4A powder (Nacalai Tesque) was added to the solution and the mixture was stirred at room temperature for 15 minutes. The reaction mixture was then cooled to −15° C. and 2.23 g of silver perchlorate anhydride was added thereto, followed by stirring at the same temperature in the dark. The reaction temperature was slowly returned to the room temperature within 2 hours and then the mixture was stirred in the dark at room temperature for one day. Separately, 500 ml of methylene chloride and 500 ml of a saturated aqueous solution of sodium hydrogencarbonate were combined together and the above-mentioned reaction mixture was added thereto at once under vigorously stirring. The mixture was vigorously stirred for 30 minutes and the insoluble matters were filtered off. The methylene chloride layer was collected and the aqueous layer was extracted twice with 300 ml portions of methylene chloride again. The organic layers were combined, washed with 600 ml of a saturated aqueous solution of sodium chloride, dried over sodium sulfate anhydride and filtered. The filtrate was concentrated under reduced pressure and the residue thus obtained was subjected to the primary purification by silica gel column chromatography [150 g, chloroform-methanol (50:1)]. Thus 57 mg of a crude compound (33) [4″-O-allyl-9-dehydro-3″-O-methyl-3-propionylleucomycin V N-oxide] was obtained.

This product was not further purified but dissolved in 4.0 ml of anhydrous methylene chloride. After adding 100 mg of triphenylphosphine, the mixture was allowed to react at room temperature for 4 days. The reaction mixture was concentrated under reduced pressure and the residue thus obtained was purified by preparative TLC [development system: chloroform-methanol (50:1), developed 4 times]. Thus 18 mg of the compound (39) was obtained.

Physicochemical Data of Compound (39)

(1) Color and form: colorless solid.
(2) Molecular formula: $C_{42}H_{67}NO_{14}$.
(3) Mass spectrum (FDMS): m/z 810 (M+H)+.
(4) Specific rotation $[\alpha]_D^{17}$ −23° (c 1.0, $CH_3OH$).
(5) m.p.: 160° C.
(6) $^1H$ NMR spectrum (400 MHz, $CDCl_3$): δ (ppm): 2.26 (br d, 2-H), 2.79 (dd, 2-H), 5.09 (br d, 3-H), 3.30 (dd, 4-H), 3.60 (s, 4-$OCH_3$), 3.89 (br d, 5-H), 1.78 (m, 6-H), 1.64 (ddd, 7-H), 6.34 (d, 10-H), 7.38 (dd, 11-H), 6.22 (m, 12-H), 6.22 (m, 13-H), 4.85 (ddq, 15-H), 1.28 (d, 16-$H_3$), 9.53 (br s, 18-H), 4.51 (d, 1′-H), 3.17 (dd, 2′-H), 3.48 (t, 4′-H), 2.60 (s, 3′-N($CH_3$)$_2$), 4.89 (d, 1″-H), 1.56 (dd, 2″-Hax), 2.23 (d, 2″-Heq), 2.87 (d, 4″-H), 4.43 (dq, 5″-H), 3.25 (s, 3″-$OCH_3$), 4.12 (br dd, 4″-$OCH_2CHCH_2$), 4.19 (br, dd, 4″-$OCH_2CHCH_2$), 5.96 (ddt, 4″-$OCH_2\underline{CH}CH_2$), 5.17 (br d, 4″-$OCH_2CH\underline{CH_2}$), 5.23 (dr d, 4″-$O\underline{CH}_2CH\underline{CH_2}$).

EXAMPLE 18

Production of Compound (40) [Compound of Formula (I) wherein $R^1$ is an Oxygen Atom, $R^2$ is a Propionyl Group, $R^3$ is a Hydrogen Atom, $R^4$ is a Methyl Group and $R^5$ is a 3-methyl-2-butenyl Group]

3.49 g of the compound (16) was dissolved in 70 ml of 1,4-dioxane. Then 70 ml of 1N hydrochloric acid was added thereto and the resulting mixture was stirred at room temperature for 1 hour and then allowed to stand at the same temperature over two days. 100 ml of a saturated aqueous solution of sodium hydrogencarbonate was slowly added to the reaction mixture and then the resulting mixture was extracted with 100 ml of methylene chloride. The aqueous layer was further extracted with 80 ml of methylene chloride again. The methylene chloride layers were combined and washed with 80 ml portions of a saturated aqueous solution of sodium chloride twice. The methylene chloride layer was dried over sodium sulfate anhydride and filtered. After concentrating the filtrate under reduced pressure, 1.95 g of a crude compound (22) [3-O-methyl-4-O-(3-methyl-2-butenyl)-L-mycarose (4-O-(3-methyl-2-butenyl)-L-cladinose)] was obtained. 1.95 g of this crude compound (22) was dissolved in 30 ml of anhydrous methylene chloride and cooled to 0° C. Separately, 2.82 g of aldolithiol-2 was dissolved in 30 ml of the same solvent. After adding 4.5 ml of tri(n-butyl)-phosphine, the mixture was cooled to the same temperature and then added dropwise to the above-mentioned solution. After allowing to react for one day at room temperature, the reaction mixture was concentrated under reduced pressure. The residue thus obtained was purified by silica gel column chromatography [400 g, chloroform] to thereby give 1.00 g of a crude compound (28) [1-deoxy-3-O-methyl-4-O-(3-methyl-2-butenyl)-1-(2-pyridylthio)-L-mycaroside (1-deoxy-4-O-(3-methyl-2-butenyl)-1-(2-pyridylthio)-L-cladinoside)]. 900 mg of this crude compound (28), which had been highly dried, and 280 mg of the compound (3) were dissolved in 3.7 ml of anhydrous acetonitrile. Then 1.4 g of an activated molecular sieve 4A powder was added to the solution and the mixture was stirred at room temperature for 15 minutes. The reaction mixture was then cooled to −15° C. and 921 mg of silver perchlorate anhydride was added thereto, followed by stirring at the same temperature in the dark. The reaction temperature was slowly returned to the room temperature within 2 hours and then the mixture was stirred in the dark at room temperature for one day. Separately, 250 ml of methylene chloride and 250 ml of a saturated aqueous solution of sodium hydrogencarbonate were combined together and the above-mentioned reaction mixture was added thereto at once under vigorously stirring. The mixture was vigorously stirred for 30 minutes and the insoluble matters were filtered off. The methylene chloride layer was collected and the aqueous layer was extracted twice with 150 ml portions of methylene chloride again. The organic layers were combined, washed with 300 ml of a saturated aqueous solution of sodium chloride, dried over sodium sulfate anhydride and filtered. The filtrate was concentrated under reduced pressure and the residue thus obtained was subjected to the primary purification by silica gel column chromatography [80 g, chloroform-methanol (50:1)]. Thus 12 mg of a crude compound (34) [9-dehydro-3″-O-methyl-4″-O-(3-methyl-2-butenyl)-3-O-propionylleucomycin V N-oxide] was obtained. This product was not further purified but dissolved in 2.0 ml of anhydrous methylene chloride. After adding 100 mg of triphenylphosphine, the mixture was allowed to react at room temperature for 5 days. The reaction mixture was concentrated under reduced pressure and the residue thus obtained was purified by preparative TLC [development system: chloroform-methanol (50:1), developed 4 times]. Thus 5.1 mg of the compound (40) was obtained.

Physicochemical Data of Compound (40)

(1) Color and form: colorless solid.
(2) Molecular formula: $C_{44}H_{71}NO_{14}$.
(3) Mass spectrum (SIMS): m/z 838 (M+H)+.
(4) Specific rotation $[\alpha]_D^{17} -12°$ (c 0.4, $CH_3OH$).
(5) m.p.: 85° C.
(6) $^1H$ NMR spectrum (400 MHz, $CDCl_3$): δ (ppm): 2.26 (br d, 2-H), 2.78 (dd, 2-H), 5.09 (br d, 3-H), 3.29 (dd, 4-H), 3.60 (s, 4-$OCH_3$), 3.89 (br d, 5-H), 6.34 (d, 10-H), 7.38 (dd, 11-H), 6.22 (m, 12-H), 6.22 (m, 13-H), 4.85 (ddq, 15-H), 1.28 (d, 16-$H_3$), 9.53 (br s, 18-H), 4.51 (d, 1'-H), 3.48 (t, 4'-H), 2.60 (s, 3'-N($CH_3$)$_2$), 4.89 (d, 1''-H), 1.56 (dd, 2''-Hax), 2.23 (d, 2''-Heq), 2.83 (d, 4''-H), 4.40 (dq, 5''-H), 3.23 (s, 3''-$OCH_3$), 4.12 (br dd, 4'''-$OCH_2CHC(CH_3)_2$), 4.16 (br dd, 4'''-$OCH_2\overline{C}HC(CH_3)_2$), 5.38 (br t, 4'''-$OCH_2CHC(C\underline{H}_3)_2$), 1.66 (s, 4'''-$OCH_2CHC(C\underline{H}_3)_2$), 1.73 (s, 4'''-$OCH_2CHC(C\underline{H}_3)_2$).

EXAMPLE 19

Production of Compound (41) [Compound of Formula (I) wherein $R^1$ is an Oxygen Atom, $R^2$ is a Propionyl Group, $R^3$ is a Hydrogen Atom, $R^4$ is a Methyl Group and $R^5$ is a Butyl Group]

3.49 g of the compound (17) was dissolved in 70 ml of 1,4-dioxane. Then 70 ml of 1N hydrochloric acid was added thereto and the thus obtained mixture was stirred at room temperature for 30 minutes and then allowed to stand at the same temperature over three days. 160 ml of a saturated aqueous solution of sodium hydrogencarbonate was slowly added to the reaction mixture and then the resulting mixture was extracted with 140 ml of methylene chloride. The aqueous layer was further extracted with 140 ml of methylene chloride again. The methylene chloride layers were combined and washed with 120 ml portions of a saturated aqueous solution of sodium chloride twice. The methylene chloride layer was dried over sodium sulfate anhydride and filtered. After concentrating the filtrate under reduced pressure, 3.15 g of a crude compound (23) [4-O-butyl-3-O-methyl-L-mycarose (4-O-butyl-L-cladinose)] was obtained.

3.15 g of this crude compound (23) was dissolved in 50 ml of anhydrous methylene chloride and cooled to 0° C. Separately, 4.78 g of aldolithiol-2 was dissolved in 50 ml of the same solvent. After adding 7.0 ml of tri(n-butyl)phosphine, the mixture was cooled to the same temperature and then added dropwise to the above-mentioned solution. After allowing to react for one day at room temperature, the reaction mixture was concentrated under reduced pressure. The residue thus obtained was purified by silica gel column chromatography [500 g, chloroform] to thereby give 2.14 g of a crude compound (29) [4-O-butyl-1-deoxy-3-O-methyl-1-(2-pyridylthio)-L-mycaroside (4-O-butyl-1-deoxy-1-(2-pyridylthio)-L-cladinoside)].

2.00 g of this crude compound (29), which had been highly dried, and 643 mg of the compound (3) were dissolved in 18 ml of anhydrous acetonitrile. Then 7.0 g of an activated molecular sieve 4A powder was added to the solution and the mixture was stirred at room temperature for 15 minutes. The reaction mixture was then cooled to −15° C. and 2.13 g of silver perchlorate anhydride was added thereto, followed by stirring at the same temperature in the dark. The reaction temperature was slowly returned to the room temperature within 2 hours and then the mixture was stirred in the dark at room temperature for one day. Separately, 500 ml of methylene chloride and 500 ml of a saturated aqueous solution of sodium hydrogencarbonate were combined together and the above-mentioned reaction mixture was added thereto at once under vigorously stirring. The mixture was vigorously stirred for 30 minutes and the insoluble matters were filtered off. The methylene chloride layer was collected and the aqueous layer was extracted twice with 300 ml portions of methylene chloride again. The organic layers were combined, washed with 600 ml of a saturated aqueous solution of sodium chloride, dried over sodium sulfate anhydride and filtered. The filtrate was concentrated under reduced pressure and the residue thus obtained was subjected to the primary purification by silica gel column chromatography [80 g, chloroform-methanol (50:1)]. Thus 41 mg of a crude compound (35) [4''-O-butyl-9-dehydro-3''-O-methyl-3-O-propionylleucomycin V N-oxide] was obtained.

This product was not further purified but dissolved in 6.0 ml of anhydrous methylene chloride. After adding 200 mg of triphenylphosphine, the mixture was allowed to react at room temperature for 6 days. The reaction mixture was concentrated under reduced pressure and the residue thus obtained was purified by preparative TLC [development system: chloroform-methanol (40:1), developed twice]. Thus 26 mg of the compound (41) was obtained.

Physicochemical Data of Compound (41)

(1) Color and form: colorless solid.
(2) Molecular formula: $C_{43}H_{71}NO_{14}$.
(3) Mass spectrum (SIMS): m/z 826 (M+H)+.
(4) Specific rotation $[\alpha]_D^{17} -22°$ (c 1.0, $CH_3OH$).
(5) m.p.: 93° C.
(6) $^1H$ NMR spectrum (400 MHz, $CDCl_3$): δ (ppm): 2.26 (br d, 2-H), 2.79 (dd, 2-H), 5.09 (br d, 3-H), 3.30 (dd, 4-H), 3.60 (s, 4-$OCH_3$), 3.89 (br d, 5-H), 1.77 (m, 6-H), 1.65 (dd, 7-H), 6.34 (d, 10-H), 7.38 (dd, 11-H), 6.22 (m, 12-H), 6.22 (m, 13-H), 4.85 (ddq, 15-H), 1.28 (d, 16-$H_3$), 9.53 (br s, 18-H), 4.51 (d, 1'-H), 3.16 (dd, 2'-H), 3.47 (t, 4'-H), 2.58 (s, 3'-N($CH_3$)$_2$), 4.88 (d, 1''-H), 1.56 (dd, 2''-Hax), 2.22 (d, 2''-Heq), 2.78 (d, 4''-H), 4.41 (dq, 5''-H), 3.25 (s, 3''-$OCH_3$), 0.91 (t, 4''-$OCH_2CH_2CH_2C\underline{H}_3$).

EXAMPLE 20

Production of Compound (42) [Compound of Formula (I) wherein $R^1$ is an Oxygen Atom, $R^2$ is a Propionyl Group, $R^3$ is a Hydrogen Atom, $R^4$ is a Methyl Group and $R^5$ is a Hexyl Group]

4.18 g of the compound (18) was dissolved in 84 ml of 1,4-dioxane. Then 84 ml of 1N hydrochloric acid was added thereto and the thus obtained mixture was stirred at room temperature over two days. 200 ml of a saturated aqueous solution of sodium hydrogencarbonate was slowly added to the reaction mixture and then the resulting mixture was extracted with 200 ml of methylene chloride. The aqueous layer was further extracted with 160 ml of methylene chloride again. The methylene chloride layers were combined and washed with 160 ml portions of a saturated aqueous solution of sodium chloride twice. The methylene chloride layer was dried over sodium sulfate anhydride and filtered. After concentrating the filtrate under reduced pressure, 4.04 g of a crude compound (24) [4-O-hexyl-3-O-methyl-L-mycarose (4-O-hexyl-L-cladinose)] was obtained.

4.04 g of this crude compound (24) was dissolved in 60 ml of anhydrous methylene chloride and cooled to 0° C. Separately, 5.94 g of aldolithiol-2 was dissolved in 60 ml of the same solvent. After adding 9.8 ml of tri(n-butyl)phosphine, the mixture was cooled to the same temperature and then added dropwise to the above-mentioned solution. After allowing to react for one day at room temperature, the reaction mixture was concentrated under reduced pressure. The residue thus obtained was purified by silica gel column chromatography [500 g, chloroform] to thereby give 2.80 g of a crude compound (30) [1-deoxy-4-O-hexyl-3-O-methyl-1-(2-pyridylthio)-L-mycaroside (1-deoxy-4-O-hexyl-1-(2-pyridylthio)-L-cladinoside)].

2.16 g of this crude compound (30), which had been highly dried, and 640 mg of the compound (3) were dissolved in 18 ml of anhydrous acetonitrile. Then 7.0 g of an activated molecular sieve 4A powder was added to the solution and the mixture was stirred at room temperature for 15 minutes. The reaction mixture was then cooled to $-15°$ C. and 2.11 g of silver perchlorate anhydride was added thereto, followed by stirring at the same temperature in the dark. The reaction temperature was slowly returned to the room temperature within 2 hours and then the mixture was stirred in the dark at room temperature for one day. Separately, 500 ml of methylene chloride and 500 ml of a saturated aqueous solution of sodium hydrogencarbonate were combined together and the above-mentioned reaction mixture was added thereto at once under vigorously stirring. The mixture was vigorously stirred for 30 minutes and the insoluble matters were filtered. The methylene chloride layer was collected and the aqueous layer was extracted twice with 300 ml portions of methylene chloride again. The organic layers were combined, washed with 600 ml of a saturated aqueous solution of sodium chloride, dried over sodium sulfate anhydride and filtered. The filtrate was concentrated under reduced pressure and the residue thus obtained was subjected to the primary purification by silica gel column chromatography [150 g, chloroform-methanol (50:1)]. Thus 45 mg of a crude compound (36) [9-dehydro-4''-O-hexyl-3''-O-methyl-3-O-propionylleucomycin V N-oxide] was obtained.

This product was not further purified but dissolved in 6.0 ml of anhydrous methylene chloride. After adding 300 mg of triphenylphosphine, the mixture was allowed to react at room temperature for 4 days. The reaction mixture was concentrated under reduced pressure and the residue thus obtained was purified by preparative TLC [development system: chloroform-methanol (40:1), developed twice]. Thus 31 mg of the compound (42) was obtained.

Physicochemical Data of Compound (42)

(1) Color and form: colorless solid.
(2) Molecular formula: $C_{45}H_{75}NO_{14}$.
(3) Mass spectrum (FDMS): m/z 854 $(M+H)^+$.
(4) Specific rotation $[\alpha]_D^{17} -19°$ (c 1.0, $CH_3OH$).
(5) m.p.: 86° C.
(6) $^1H$ NMR spectrum (400 MHz, $CDCl_3$): δ (ppm): 2.28 (br d, 2-H), 2.81 (dd, 2-H), 5.11 (br d, 3-H), 3.31 (dd, 4-H), 3.62 (s, 4-$OCH_3$), 3.91 (br d, 5-H), 1.79 (m, 6-H), 1.66 (ddd, 7-H), 6.36 (d, 10-H), 7.40 (dd, 11-H), 6.24 (m, 12-H), 6.24 (m, 13-H), 4.87 (ddq, 15-H), 9.55 (br s, 18-H), 4.53 (d, 1'-H), 3.18 (dd, 2'-H), 3.49 (t, 4'-H), 2.61 (s, 3'-N($CH_3$)$_2$), 4.90 (d, 1''-H), 1.58 (dd, 2''-Hax), 2.24 (d, 2''-Heq), 2.80 (d, 4''-H), 4.42 (dq, 5''-H), 3.27 (s, 3''-$OCH_3$), 0.90 (t, 4''-$OCH_2CH_2CH_2CH_2CH_2CH_3$).

EXAMPLE 21

Production of Compound (43) [Compound of Formula (I) wherein $R^1$ is an Oxygen Atom, $R^2$ is a Propionyl Group, $R^3$ is a Hydrogen Atom, $R^4$ is a Methyl Group and $R^5$ is a 4-methylpentyl Group]

3.44 g of the compound (19) was dissolved in 70 ml of 1,4-dioxane. Then 70 ml of 1N hydrochloric acid was added thereto and the thus obtained mixture was stirred at room temperature over two days. 160 ml of a saturated aqueous solution of sodium hydrogencarbonate was slowly added to the reaction mixture and then the resulting mixture was extracted with 140 ml of methylene chloride. The aqueous layer was further extracted with 140 ml of methylene chloride again. The methylene chloride layers were combined and washed with 120 ml portions of a saturated aqueous solution of sodium chloride twice. The methylene chloride layer was dried over sodium sulfate anhydride and filtered. After concentrating the filtrate under reduced pressure, 3.20 g of a crude compound (25) [3-O-methyl-4-O-(4-methylpentyl)-L-mycarose (4-O-(4-methylpentyl)-L-cladinose)] was obtained.

3.20 g of this crude compound (25) was dissolved in 40 ml of anhydrous methylene chloride and cooled to 0° C. Separately, 4.30 g of aldolithiol-2 was dissolved in 40 ml of the same solvent. After adding 6.0 ml of tri(n-butyl)phosphine, the mixture was cooled to the same temperature and then added dropwise to the above-mentioned solution. After allowing to react for one day at room temperature, the reaction mixture was concentrated under reduced pressure. The residue thus obtained was purified by silica gel column chromatography [500 g, n-hexane-chloroform-ethyl acetate (5:2:1)] to thereby give 1.11 g of a crude compound (31) [1-deoxy-3-O-methyl-4-O-(4-methylpentyl)-1-(2-pyridylthio)-L-mycaroside (1-deoxy-4-O-(4-methylpentyl)-1-(2-pyridylthio)-L-cladinoside)].

1.00 g of this crude compound (31), which had been highly dried, and 296 mg of the compound (3) were dissolved in 9.0 ml of anhydrous acetonitrile. Then 1.5 g of an activated molecular sieve 4A powder was added to the solution and the mixture was stirred at room temperature for 15 minutes. The reaction mixture was then cooled to $-15°$ C. and 970 mg of silver perchlorate anhydride was added thereto, followed by stirring at the same temperature in the dark. The reaction temperature was slowly returned to the room temperature within 2 hours and then the mixture was stirred in the dark at room temperature for one day. Separately, 250 ml of methylene chloride and 250 ml of a saturated aqueous solution of sodium hydrogencarbonate were combined together and the above-mentioned reaction mixture was added thereto at once under vigorously stirring. The mixture was vigorously stirred for 30 minutes and the insoluble matters were filtered off. The methylene chloride layer was collected and the aqueous layer was extracted twice with 150 ml portions of methylene chloride again. The organic layers were combined, washed with 300 ml of a saturated aqueous solution of sodium chloride, dried over sodium sulfate anhydride and filtered. The filtrate was concentrated under reduced pressure and the residue thus obtained was subjected to the primary purification by silica gel column chromatography [80 g, chloroform-methanol (50:1)]. Thus 28 mg of a crude compound (37) [9-dehydro-3''-O-methyl-4''-O-(4-methylpentyl)-3-O-propionylleucomycin V N-oxide] was obtained.

This product was not further purified but dissolved in 4.0 ml of anhydrous methylene chloride. After adding 200 mg of triphenylphosphine, the mixture was allowed to react at room temperature for 3 days. The reaction mixture was concentrated under reduced pressure and the residue thus obtained was purified by preparative TLC [development system: chloroform-methanol (40:1), developed twice]. Thus 20 mg of the compound (43) was obtained.

Physicochemical Data of Compound (43)

(1) Color and form: colorless solid.
(2) Molecular formula: $C_{45}H_{75}NO_{14}$.
(3) Mass spectrum (FDMS): m/z 854 (M+H)+.
(4) Specific rotation $[\alpha]_D^{17} -17°$ (c 1.0, $CH_3OH$).
(5) m.p.: 92°–94° C.
(6) $^1H$ NMR spectrum (400 MHz, $CDCl_3$): δ (ppm): 2.25 (br d, 2-H), 2.79 (dd, 2-H), 5.09 (br d, 3-H), 3.30 (dd, 4-H), 3.60 (s, 4-$OCH_3$), 3.88 (br d, 5-H), 1.78 (m, 6-H), 1.65 (ddd, 7-H), 6.34 (d, 10-H), 7.38 (dd, 11-H), 6.21 (m, 12-H), 6.21 (m, 13-H), 4.85 (ddq, 15-H), 1.28 (d, 16-$H_3$), 9.54 (br s, 18-H), 4.51 (d, 1'-H), 3.17 (dd, 2'-H), 3.47 (t, 4'-H), 2.60 (s, 3'-N($CH_3$)$_2$), 4.88 (d, 1''-H), 1.56 (dd, 2''-Hax), 2.22 (d, 2''-Heq), 2.77 (d, 4''-H), 4.40 (dq, 5''-H), 3.25 (s, 3''-$OCH_3$), 0.87 (d, 4''-$OCH_2CH_2CH_2CH(CH_3)_2$).

EXAMPLE 22

Production of Compound (44) [Compound of Formula (I) wherein $R^1$ is an Oxygen Atom, $R^2$ is a Propionyl Group, $R^3$ is a Hydrogen Atom, $R^4$ is a Methyl Group and $R^5$ is a Benzyl Group]

3.51 g of the compound (20) was dissolved in 70 ml of 1,4-dioxane. Then 70 ml of 1N hydrochloric acid was added thereto and the thus obtained mixture was stirred at 35° C. overnight and then heated to 50° C. for 1 hour. 160 ml of a saturated aqueous solution of sodium hydrogencarbonate was slowly added to the reaction mixture and then the resulting mixture was extracted with 140 ml of methylene chloride. The aqueous layer was further extracted with 140 ml of methylene chloride again. The methylene chloride layers were combined and washed with 120 ml portions of a saturated aqueous solution of sodium chloride twice. The methylene chloride layer was dried over sodium sulfate anhydride and filtered. After concentrating the filtrate under reduced pressure, 3.33 g of a crude compound (26) [4-O-benzyl-3-O-methyl-L-mycarose (4-O-benzyl-L-cladinose)] was obtained.

3.33 g of this crude compound (26) was dissolved in 50 ml of anhydrous methylene chloride and cooled to 0° C. Separately, 4.40 g of aldolithiol-2 was dissolved in 50 ml of the same solvent. After adding 6.4 ml of tri(n-butyl)phosphine, the mixture was cooled to the same temperature and then added dropwise to the above-mentioned solution. After allowing to react for one day at room temperature, the reaction mixture was concentrated under reduced pressure. The residue thus obtained was purified by silica gel column chromatography [500 g, chloroform-ethyl acetate (100:1)] to thereby give 2.80 g of a crude compound (32) [4-O-benzyl-1-deoxy-3-O-methyl-1-(2-pyridylthio)-L-mycaroside (4-o-benzyl-1-deoxy-1-(2-pyridylthio)-L-cladinoside)].

2.10 g of this crude compound (32), which had been highly dried, and 611 mg of the compound (3) were dissolved in 18 ml of anhydrous acetonitrile. Then 7.0 g of an activated molecular sieve 4A powder was added to the solution and the mixture was stirred at room temperature for 15 minutes. The reaction mixture was then cooled to −15° C. and 2.00 g of silver perchlorate anhydride was added thereto, followed by stirring at the same temperature in the dark. The reaction temperature was slowly returned to the room temperature within 2 hours and then the mixture was stirred in the dark at room temperature for one day. Separately, 500 ml of methylene chloride and 500 ml of a saturated aqueous solution of sodium hydrogencarbonate were combined together and the above-mentioned reaction mixture was added thereto at once under vigorously stirring. The mixture was vigorously stirred for 30 minutes and the insoluble matters were filtered off. The methylene chloride layer was collected and the aqueous layer was extracted twice with 300 ml portions of methylene chloride again. The organic layers were combined, washed with 600 ml of a saturated aqueous solution of sodium chloride, dried over sodium sulfate anhydride and filtered. The filtrate was concentrated under reduced pressure and the residue thus obtained was subjected to the primary purification by silica gel column chromatography [80 g, chloroform-methanol (50:1)]. Thus 73 mg of a crude compound (38) [4''-O-benzyl-9-dehydro-3''-O-methyl-3-O-propionylleucomycin V N-oxide] was obtained. This product was not further purified but dissolved in 6.0 ml of anhydrous methylene chloride. After adding 500 mg of triphenylphosphine, the mixture was allowed to react at room temperature for 5 days. The reaction mixture was concentrated under reduced pressure and the residue thus obtained was purified by preparative TLC [development system: chloroform-methanol (50:1), developed twice]. Thus 42 mg of the compound (44) was obtained.

Physicochemical Data of Compound (44)

(1) Color and form: colorless solid.
(2) Molecular formula: $C_{46}H_{69}NO_{14}$.
(3) Mass spectrum (FDMS): m/z 860 (M+H)+.
(4) Specific rotation $[\alpha]_D^{17} -14°$ (c1.0, $CH_3OH$).
(5) m.p.: 95°–97° C.
(6) $^1H$ NMR spectrum (400 MHz, $CDCl_3$): δ (ppm): 2.26 (br d, 2-H), 2.79 (dd, 2-H), 5.09 (br d, 3-H), 3.29 (dd, 4-H), 3.60 (s, 4-$OCH_3$), 3.89 (br d, 5-H), 1.78 (m, 6-H), 1.65 (ddd, 7-H), 6.34 (d, 10-H), 7.38 (dd, 11-H), 6.21 (m, 12-H), 6.21 (m, 13-H), 4.85 (ddq, 15-H), 1.28 (d, 16-$H_3$), 9.52 (br s, 18-H), 4.50 (d, 1'-H), 3.16 (dd, 2'-H), 3.47 (t, 4'-H), 2.56 (s, 3'-N($CH_3$)$_2$), 4.89 (d, 1''-H), 1.56 (dd, 2''-Hax), 2.21 (d, 2''-Heq), 2.99 (d, 4''-H), 4.48 (dq, 5''-H), 3.25 (s, 3''-$OCH_3$), 4.62 (d, 4''-$OCH_2C_6H_5$), 4.70 (d, 4''-$OCH_2C_6H_5$), 7.34 (m, 4''-$OCH_2C_6\underline{H}_5$).

While the invention has been described in detail and with reference to specific embodiments thereof, it will be appaent to one skilled in the art that various changes and modifications can be made therein without departing from the spirit and scope thereof.

What is claimed is:

1. A compound represented by the formula (I):

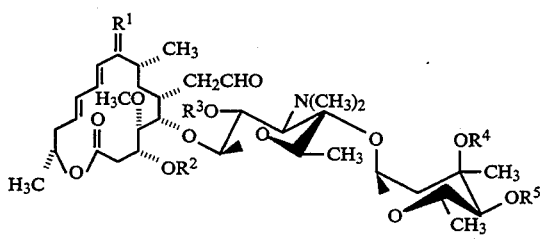

wherein $R^1$ represents an oxygen atom, a hydroxyl group and a hydrogen atom or a group of the formula $OCOR^6$, wherein $R^6$ represents a straight chain alkyl group having 1 to 3 carbon atoms, and a hydrogen atom, $R^2$ represents a hydrogen atom or a group of the formula $COR^6$, wherein $R^6$ is as defined above, $R^3$ represents a hydrogen atom or a group of $COR^6$, wherein $R^6$ is as defined above, $R^4$ represents a straight chain alkyl group having 1 to 4 carbon atoms, and $R^5$ represents a substituted or unsubstituted straight chain or branched alkyl or aralkyl group having 1 to 10 carbon atoms, or a pharmaceutically acceptable salt thereof.

2. A compound represented by the formula (I) as claimed in claim 1, wherein $R^1$ is an oxygen atom, $R^2$ is a propionyl group, $R^3$ is a hydrogen atom, $R^4$ is a methyl group and $R^5$ is an ethyl group, or a pharmaceutically acceptable salt thereof.

3. A compound represented by the formula (I) as claimed in claim 1, wherein $R^1$ is an oxygen atom, $R^2$ is a propionyl group, $R^3$ is a hydrogen atom, $R^4$ is a methyl group and $R^5$ is an isoamyl group, or a pharmaceutically acceptable salt thereof.

4. A compound represented by the formula (I) as claimed in claim 1, wherein $R^1$ is an oxygen atom, $R^2$ is a propionyl group, $R^3$ is a hydrogen atom, $R^4$ is a methyl group and $R^5$ is an allyl(2-propenyl) group, or a pharmaceutically acceptable salt thereof.

5. A compound represented by the formula (I) as claimed in claim 1, wherein $R^1$ is an oxygen atom, $R^2$ is a propionyl group, $R^3$ is a hydrogen atom, $R^4$ is a methyl group and $R^5$ is a 3-methyl-2-butenyl group, or a pharmaceutically acceptable salt thereof.

6. A compound represented by the formula (I) as claimed in claim 1, wherein $R^1$ is an oxygen atom, $R^2$ is a propionyl group, $R^3$ is a hydrogen atom, $R^4$ is a methyl group and $R^5$ is a butyl group, or a pharmaceutically acceptable salt thereof.

7. A compound represented by the formula (I) as claimed in claim 1, wherein $R^1$ is an oxygen atom, $R^2$ is a propionyl group, $R^3$ is a hydrogen atom, $R^4$ is a methyl group and $R^5$ is a hexyl group, or a pharmaceutically acceptable salt thereof.

8. A compound represented by the formula (I) as claimed in claim 1, wherein $R^1$ is an oxygen atom, $R^2$ is a propionyl group, $R^3$ is a hydrogen atom, $R^4$ is a methyl group and $R^5$ is a 4-methylpentyl group, or a pharmaceutically acceptable salt thereof.

9. A compound represented by the formula (I) as claimed in claim 1, wherein $R^1$ is an oxygen atom, $R^2$ is a propionyl group, $R^3$ is a hydrogen atom, $R^4$ is a methyl group and $R^5$ is a benzyl group, or a pharmaceutically acceptable salt thereof.

10. A compound represented by the formula (II):

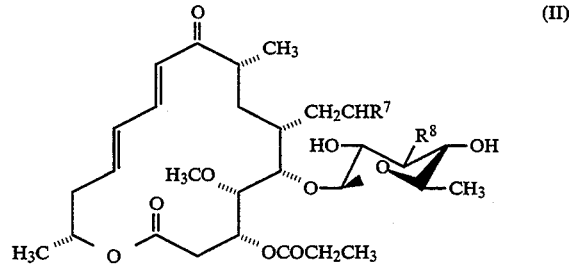

wherein $R^7$ represents an oxygen atom, a group of the formula $-O(CH_2)_nO-$, wherein n is an integer of 2 or 3, a group of the formula $=(OR^9)_2$, wherein $R^9$ represents an alkyl group having 1 to 4 carbon atoms or a benzyl group, a group of the formula $-S(CH_2)_nS-$, wherein n is an integer of 2 or 3, or a group of the formula $=(SR^9)_2$, wherein $R^9$ is as defined above, and $R^8$ is a dimethylamino group or a dimethylamino group N-oxide provided that $R^8$ is not a dimethylamino group when $R^7$ is an oxygen atom, or a salt thereof.

11. A compound represented by the formula (II) as claimed in claim 10, wherein $R^7$ is an ethylenedioxy group and $R^8$ is a dimethylamino group.

12. A compound represented by the formula (II) as claimed in claim 10, wherein $R^7$ is an ethylenedioxy group and $R^8$ is a dimethylamino group N-oxide.

13. A compound represented by the formula (II) as claimed in claim 10, wherein $R^7$ is an oxygen atom and $R^8$ is a dimethylamino group N-oxide.

* * * * *